United States Patent
Howard et al.

(10) Patent No.: US 9,364,660 B2
(45) Date of Patent: Jun. 14, 2016

(54) ELECTRODE ARRAY DEVICE CONFIGURED FOR PLACEMENT INSIDE THE DURA FOR DIRECT SPINAL CORD STIMULATION

(75) Inventors: Matthew Howard, Iowa City, IA (US); Timothy Brennan, Iowa City, IA (US); Brian Dalm, Coralville, IA (US); Marcel Utz, Charlottesville, VA (US); George T. Gillies, Charlottesville, VA (US); Steven Scott, Excelsior, MN (US); Randall S. Nelson, Pine Springs, MN (US); Robert Shurig, Saint Paul, MN (US)

(73) Assignees: University of Iowa Research Foundation, Iowa City, IA (US); University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 13/885,157
(22) PCT Filed: Nov. 11, 2011
(86) PCT No.: PCT/US2011/060462
§ 371 (c)(1),
(2), (4) Date: Jan. 6, 2014
(87) PCT Pub. No.: WO2012/065125
PCT Pub. Date: May 18, 2012

(65) Prior Publication Data
US 2014/0128955 A1 May 8, 2014

Related U.S. Application Data

(60) Provisional application No. 61/412,651, filed on Nov. 11, 2010.

(51) Int. Cl.
*A61N 1/05* (2006.01)
*A61N 1/36* (2006.01)
(Continued)

(52) U.S. Cl.
CPC ............ *A61N 1/0553* (2013.01); *A61N 1/0558* (2013.01); *A61N 1/36071* (2013.01);
(Continued)

(58) Field of Classification Search
CPC .. A61N 1/0558; A61N 1/36071; A61N 1/372
See application file for complete search history.

(56) References Cited

U.S. PATENT DOCUMENTS 3,612,061 A * 10/1971 Collins ..................... A61F 9/08
340/407.1
3,724,467 A * 4/1973 Avery ..................... A61N 1/375
607/117

(Continued)

FOREIGN PATENT DOCUMENTS

CN 101048194 A 10/2007
WO 95/32677 A1 12/1995

(Continued)

OTHER PUBLICATIONS

International Preliminary Report on Patentability for International Application No. PCT/US2011/060462 issued May 14, 2013, 11 pages.

(Continued)

*Primary Examiner* — William Levicky
(74) *Attorney, Agent, or Firm* — Kilpatrick Townsend and Stockton LLP

(57) ABSTRACT

A method for treating intractable pain via electrical stimulation of the spinal cord. Remote, non-contact stimulation of a selected region of spinal cord is achieved by placement of a transceiver patch directly on the surface of that region of spinal cord, with said patch optionally being inductively coupled to a transmitter patch of similar size on either the outer or inner wall of the dura surrounding that region of the spinal cord. By inductively exchanging electrical power and signals between said transmitter and transceiver patches, and by carrying out the necessary electronic and stimulus signal distribution functions on the transceiver patch, the targeted dorsal column axons can be stimulated without the unintended stray stimulation of nearby dorsal rootlets. Novel configurations of a pliable surface-sheath and clamp or dentate ligament attachment features which realize undamaging attachment of the patch to the spinal cord are described.

21 Claims, 32 Drawing Sheets

(51) Int. Cl.
*A61N 1/372* (2006.01)
*A61N 1/375* (2006.01)
*A61N 1/378* (2006.01)

(52) U.S. Cl.
CPC ............... *A61N1/372* (2013.01); *A61N 1/375* (2013.01); *A61N 1/3787* (2013.01); *A61N 1/37205* (2013.01); *Y10T 29/49117* (2015.01)

(56) References Cited

U.S. PATENT DOCUMENTS

| | | | |
|---|---|---|---|
| 3,822,708 A | 7/1974 | Zilber | |
| 4,549,556 A * | 10/1985 | Tarjan | A61N 1/0558 607/117 |
| 4,590,946 A | 5/1986 | Loeb | |
| 4,837,049 A * | 6/1989 | Byers | A61B 5/0422 216/11 |
| 6,175,769 B1 | 1/2001 | Errico et al. | |
| 6,295,472 B1 | 9/2001 | Rubinstein et al. | |
| 6,319,241 B1 | 11/2001 | King et al. | |
| 6,549,810 B1 | 4/2003 | Leonard et al. | |
| 6,631,295 B2 | 10/2003 | Rubinstein et al. | |
| 7,333,857 B2 * | 2/2008 | Campbell | 607/46 |
| 7,337,006 B2 * | 2/2008 | Kim et al. | 607/46 |
| 7,769,472 B2 * | 8/2010 | Gerber | 607/118 |
| 8,209,021 B2 | 6/2012 | Alataris et al. | |
| 8,295,945 B1 | 10/2012 | Thacker et al. | |
| 8,649,874 B2 | 2/2014 | Alataris et al. | |
| 8,712,533 B2 | 4/2014 | Alataris et al. | |
| 2002/0111660 A1 | 8/2002 | Errico et al. | |
| 2003/0204228 A1 | 10/2003 | Cross et al. | |
| 2004/0176831 A1 * | 9/2004 | Gliner | A61N 1/0531 607/142 |
| 2005/0131506 A1 | 6/2005 | Rezai et al. | |
| 2007/0073357 A1 | 3/2007 | Rooney et al. | |
| 2008/0234791 A1 | 9/2008 | Arle et al. | |
| 2009/0281599 A1 | 11/2009 | Thacker et al. | |
| 2010/0057177 A1 * | 3/2010 | Moffitt | A61N 1/0553 607/117 |
| 2010/0063568 A1 * | 3/2010 | Staunton | A61N 1/0551 607/116 |
| 2010/0100165 A1 | 4/2010 | Swanson et al. | |
| 2010/0145428 A1 | 6/2010 | Cameron et al. | |
| 2010/0204766 A1 * | 8/2010 | Zdeblick | A61B 5/0422 607/119 |
| 2011/0224755 A1 | 9/2011 | Arle et al. | |
| 2012/0016438 A1 | 1/2012 | Alataris et al. | |
| 2014/0371830 A1 | 12/2014 | Howard et al. | |
| 2014/0379043 A1 | 12/2014 | Howard | |

FOREIGN PATENT DOCUMENTS

| | | |
|---|---|---|
| WO | 2006/029257 A2 | 3/2006 |
| WO | 2010/124139 A1 | 10/2010 |
| WO | 2012/065125 A1 | 5/2012 |
| WO | 2013/116368 A1 | 8/2013 |
| WO | 2013/116377 A1 | 8/2013 |

OTHER PUBLICATIONS

Extended European Search Report for EP Application No. 11839545.8 mailed Apr. 24, 2014.
"Nevro Corp. Announces Publication of Positive Six-Month Clinical Data for Senza HF10™ High-Frequency Spinal Cord Stimulation Therapy in Europe," Nevro Newsroom Press Release dated Feb. 6, 2013, downloaded from http://www.nevro.com/nevro-corp-announces-publication-of-positive-six-month-clinical-data-for-senza-hf10-high-frequency-spinal-cord-stimulation-therapy-in-europe/ , last visited on Jan. 4, 2015.
Eldabe et al., "An Analysis of the Components of Pain, Function, and Health-Related Quality of Life in Patients with Failed Back Surgery Syndrome Treated with Spinal Cord Stimulation or Conventional Medical Management," Neuromodulation 13(3): 201-209 (2010).
Gibson-Corley et al., "Ovine Tests of a Novel Spinal Cord Neuromodulator and Dentate Ligament Fixation Method," Journal of Investigative Surgery 25(6): 366-374 (2012). (Abstract Only).
Gibson-Corley et al., "Postsurgical Pathologies Associated with Intradural Electrical Stimulation in the Central Nervous System: Design Implications for a New Clinical Device," BioMed Research International 2014, Article ID No. 989175 (2014).
International Search Report and Written Opinion for PCT Application No. PCT/US2011/060462 mailed Mar. 2, 2012.
International Search Report and Written Opinion for PCT Application No. PCT/US2013/023897 mailed Apr. 16, 2013.
International Search Report and Written Opinion for PCT Application No. PCT/US2013/023912 mailed Jun. 4, 2013.
Oliynyk et al., "Dynamic Loading Characteristics of an Intradural Spinal Cord Stimulator," Journal of Applied Physics 113: 026103 (2013).
Oya et al., "Soft-Coupling Suspension System for an Intradural Spinal Cord Stimulator: Biophysical Performance Characteristics," Journal of Applied Physics 114: 164701 (2013).
Viljoen et al., "MR-Based Measurement of Spinal Cord Motion During Flexion of the Spine: Implications for Intradural Spinal Cord Stimulator Systems," Journal of Medical Engineering and Technology 38(1): 1-4 (2014). (Abstract Only).
Wilson et al., "Pulsatile Spinal Cord Surrogate for Intradural Neuromodulation Studies," Journal of Medical Engineering and Technology 36(1): 22-25 (2012). (Abstract Only).
International Search Report and Written Opinion of the International Searching Authority mailed on Dec. 23, 2014 for PCT Patent Application No. PCT/US2014/054243, 13 pages.
Sweet, W.H. et al. (1974). "Stimulation of the Posterior Columns of the Spinal Cord for Pain Control: Indications, Technique, and Results," *Clinical Neurosurgery* 21:278-310.
Chinese Office Action mailed on Sep. 19, 2014 for CN Application No. 201180064806.1, 16 pages.
Flouty et al., "A new device concept for directly modulating spinal cord pathways: initial in vivo experimental results", Physiol Meas. Dec. 2012;33(12):2003-15.
Gibson-Corley et al., "Ovine tests of a novel spinal cord neuromodulator and dentate ligament fixation method", J Invest Surg. Dec. 2012;25(6):366-74.
Long, "Electrical Stimulation for the Control of Pain", Symposium on Pain, Arch Surg., Jul. 1977; 112(7), 884-8.
Oya et al., "Applier tool for intradural spinal cord implants", J Med Eng Technol. Apr. 2012;36(3):169-73.
Oya et al., "Spinal canal surrogate for testing intradural implants", J Med Eng Technol. Nov. 2012;36(8):407-10.
Safayi et al., "Biomechanical performance of an ovine model of intradural spinal cord stimulation", J Med Eng Technol. Jul. 2014;38(5):269-73.
Song et al., "Power and signal transmission protocol for a contactless subdural spinal cord stimulation device", Biomed Microdevices. Feb. 2013;15(1):27-36.
Viljoen et al., "Apparatus for simulating dynamic interactions between the spinal cord and soft-coupled intradural implants", Rev Sci Instrum. Nov. 2013;84(11):114303.
Viljoen et al., "MR-based measurement of spinal cord motion during flexion of the spine: implications for intradural spinal cord stimulator systems", J Med Eng Technol. Jan. 2014;38(1):1-4.
Wilson et al., "Pulsatile spinal cord surrogate for intradural neuromodulation studies", J Med Eng Technol. Jan. 2012;36(1):22-5.
Burton, "Safety and Clinical Efficacy of Implanted Neuroaugmentive Spinal Devices for the Relief of Pain", Appl. Neurophysiol. 1977-78;40:175-83.
Flouty et al., "Intracranial Somatosensory Responses with Direct Spinal Cord Stimulation in Anesthetized Sheep", PLOS ONE, Feb. 2013, vol. 8, e56266, pp. 1-11.
Gibson-Corley et al., "Postsurgical Pathologies Associated with Intradural Electrical Stimulation in the Central Nervous System: Design Implications for a New Clinical Device", BioMed Research International, vol. 2014, Article ID 989175, 10 pages.
Gildenberg PL, "Evolution of Spinal Cord Surgery for Pain", Clinical Neurosurgery, 2006; 53:11-7.

(56) References Cited

OTHER PUBLICATIONS

Howell et al., "Evaluation of Intradural Stimulation Efficiency and Selectivity in a Computational Model of Spinal Cord Stimulation", PLoS ONE 9(12): e114938, 1-25.

Huang et al., "Comparison of spinal cord stimulation profiles from intra- and extradural electrode arrangements by finite element modeling", Med Biol Eng Comput (2014) 52:531-538.

Long, "The Current Status of Electrical Stimulation of the Nervous System for the Relief of Chronic Pain", Surg Neurol, Feb. 1998; 49(2); 142-4.

Mayfield Clinic & Spine Institute, "Spinal Cord Stimulation, advanced level", accessible on www.mayfieldclinic.com, 2002, 6 pages.

Shealy et al., "Dorsal Column Electroanalgesia", J. Neurosurg., May 1970;32(5), 560-4.

* cited by examiner

Malleable Full-Circumference I-Patch Variant

Intra-Dural Relay Device (IDRD)

ELECTRODE ARRAY DEVICE CONFIGURED FOR PLACEMENT INSIDE THE DURA FOR DIRECT SPINAL CORD STIMULATION

CROSS REFERENCE TO RELATED APPLICATION DATA

The present application claims the benefit of U.S. Provisional Appln No. 61/412,651 filed Nov. 11, 2010; the full disclosure of which is incorporated herein by reference in its entirety for all purposes.

BACKGROUND OF THE INVENTION

Field of the Invention

The present invention relates generally to medical devices and methods. More particularly, the present invention relates to electrode structures and systems for delivering electrical pulses directly to the spinal cord of a patient to block pain and for other purposes.

The use of spinal cord stimulation (SCS) to relieve intractable pain symptoms originated in the 1960's along with emerging theories of the neural basis of pain perception and the pathophysiology of chronic pain disorders. Results from experimental animal studies demonstrated the existence of neural pathways that originate within the brain and project axons through the spinal cord that eventually terminate at spinal cord levels where pain signals from the peripheral nervous system enter the central nervous system. These pathways are postulated to play a role in the 'top-down' modulation of pain perception. Human SCS studies were initiated based on the theory that by using electrical stimulation to artificially activate descending pathways within the dorsal column of the spinal cord, the processing of pain related signals below the stimulation site could be attenuated, blocked or otherwise modulated.

Although the specific neural mechanisms that underlie the clinical efficacy of this treatment remain poorly understood, there is now abundant clinical evidence that SCS is capable of providing sustained pain relief to select patients with intractable chronic pain. The most important limitation of this treatment method is that a high percentage of patients implanted with an SCS system or device may experience only marginal improvement, or no improvement, in their pain symptoms. Treatment success rates of 50% or less are frequently reported with known SCS systems.

The neural mechanisms that mediate the clinical effects of SCS are complex and likely involve activation of multiple ascending and descending neural pathways within the spinal cord. Based on empiric clinical evidence, a number of treatment concepts have emerged to guide SCS strategies. In general, electrical stimulation will evoke sensory perceptions in the painful area of the body in order for the treatment to be effective. To accomplish this, the region within the dorsal column of the spinal cord that contains axons that are functionally related to the painful body area must be activated. Dorsal column axons are somatotopically organized, meaning that the axons that are functionally related to a particular body area are positioned in close proximity to each other, and there is an orderly anatomical pattern of organization within the spinal cord for the different groups of axons linked to different body areas. In the cervical spinal cord, for example, dorsal column axons functionally linked to the back region may be relatively close to the midline of the spinal cord, and axons linked to the arms are positioned relatively more laterally.

Adverse effects of electrical stimulation can result from unintended activation of non-targeted neural structures. When the dorsal nerve rootlets are activated, for example, discomfort can result. The effectiveness of SCS treatment is generally dependent on the capacity of the device to selectively activate targeted axons within a specific sub-region of the dorsal column, without activating the nearby dorsal rootlets. This concept is incorporated into researcher's use of the term therapeutic range to describe the range of stimulus intensities that are above perceptual threshold (i.e. effectiveness threshold) but below the discomfort threshold, beyond which stimulation effects are no longer tolerated by the patient. The ideal SCS device will be capable of efficiently and safely delivering highly focused electrical stimuli to the targeted sub-region of the dorsal column without activating nearby structures. The electrode contact should be positioned as close to the targeted axons as possible and the resulting volumetric pattern of tissue activation should tightly conform to the anatomy of the targeted neural pathway.

The spinal cord is cylindrically shaped and positioned centrally within the spinal canal. The spinal canal is lined by a dural membrane and contains cerebrospinal fluid (CSF) that surrounds the spinal cord and fills the region between the outside surface of the spinal cord and the inside surface of the dural membrane. This CSF-filled space plays a critical role in normal spinal cord biomechanics and is an important factor that should be considered when performing spinal surgery. During normal movements, such as flexion and extension of the body, the spinal cord moves within the spinal canal, altering its position relative to the dural lining of the spinal canal. The volume of CSF surrounding the spinal cord serves as a frictionless buffer during these movements. In some pathological conditions (e.g. tethered cord syndrome) this normal motion of the spinal cord is impeded by tissue attachments bridging the space between the spinal cord and the dural lining, resulting in dysfunction of the spinal cord. In other pathological conditions, a tissue barrier forms within the spinal canal (e.g. following trauma or infection) that disrupts the normal flow of CSF over the surface of the spinal cord. In this setting CSF may accumulate within the substance of the spinal cord to form a syrinx and cause neurological dysfunction.

The dural lining of the spinal canal should be managed with particular care during spinal surgery. If a defect is created in this lining, a CSF fistula may develop which increases the risk of a wound complication (infection or dehiscence) and may cause the patient to experience disabling positional headaches. In order to access the spinal cord itself, the dural membrane should be opened surgically and this is performed in a manner that allows the surgeon to achieve a 'water-tight' closure at the completion of the operation. Typically this involves sharply incising the dura over the dorsal aspect of the spinal canal, a location that is readily accessible and well visualized during surgery. Later the dura is re-approximated by suturing together the well defined cut margins of the fibrous membrane. This closure technique is performed in a manner that preserves the CSF filled space separating the dura from the spinal cord, thus preventing mechanical constriction, or tethering, at the surgical site.

These anatomical and surgical considerations have impacted the evolution of a wide range of operative procedures, including spinal cord stimulator surgery. When the design intent is to minimize the risk of surgical complications, the optimal strategy is to entirely avoid opening the dural membrane and place the implant outside of the dura (extra-dural procedure). If the spinal cord must be accessed directly (intra-dural procedure) the operation should be designed in a manner that prevents CSF fistula formation, mechanical tethering of the spinal cord to the dura, or physical obstruction of the CSF filled space surrounding the spinal cord.

There are limitations in the performance characteristics of the prior art. One such limitation is the following. Existing SCS devices deliver electrical stimuli through electrodes placed outside of the fibrous lining of the spinal canal (dura). This results in inefficient and poorly localized patterns of spinal cord activation due to the electrical shunting effect of cerebrospinal fluid that fills the space separating the dural lining and the spinal cord. This inability to selectively activate targeted regions of the spinal cord is thought to be an important contributing factor to the significant incidence of suboptimal or poor treatment outcomes with existing SCS devices. Despite these limitations large numbers of patients are implanted. The size of the SCS market attests to the large scope of this public health problem and the fact that under certain circumstances, electrical activation of the spinal cord provides pain relief for patients who have failed all other treatment modalities.

A further limitation of the prior art arises in the nature of certain tethered forms of spinal cord stimulators. When SCS electrodes were first placed in human subjects, most were implanted on the surface of the dura, but in some instances the dura was opened and electrodes were placed directly on the surface (intradural) of the spinal cord (Gildenberg 2006, Long 1977, Long 1998, Shealy et al. 1970). The wires from electrodes placed directly on the spinal cord passed through the dura, thus mechanically tethering the electrode to the dura. The electrodes were constructed of conventional conductive and insulting materials, were bulky, and had a limited number of contacts through which stimuli could be delivered. The locations of the contacts relative to targeted and non-targeted neural structures were difficult to control and could not be adjusted following the implantation surgery. Because of these factors, and the increased risks associated with opening the dura, at the time there was no obvious therapeutic advantage to the intradural approach. The use of intradural stimulating electrodes was eventually discontinued and currently all SCS devices use extradural stimulating electrodes.

Still another limitation of the prior art arises in terms of the treatment efficacy. There are two broad classes of extradural stimulation electrodes. One type can be placed percutaneously through a needle into the epidural space. These electrodes have small cylindrically shaped contacts positioned along the shaft of a flexible linear electrode array. They are used either for minimally invasive testing of stimulation effects prior to implantation surgery, or as the device that is permanently implanted. The other type of extradural electrode is placed during an open surgical procedure and consists of a flat array of multiple electrode contacts positioned over the exposed dural surface. An experienced practitioner is capable of implanting these extradural electrodes with a high degree of safety. However, the current SCS devices have suboptimal treatment efficacy. We hypothesize that this shortcoming is due in large part to the inability of extradural electrodes to selectively activate the targeted sub-region of the dorsal column of the spinal cord. By placing devices outside of the dura because of safety considerations, an intrinsic disadvantage is incurred in terms of therapeutic efficacy. The presence of a CSF filled space between an extradural stimulating electrode and the spinal cord profoundly degrades the ability of the device to create a volume of electrical activation that selectively encompasses the targeted sub-region of the spinal cord. This results from the conductive properties of CSF. CSF is a far more efficient electrical conductor than any other tissue in the spine (Holsheimer 1998). When an electrical stimulus delivered by an extradural electrode traverses the dura and enters the CSF-filled space between the dura and the spinal cord, a large fraction of the stimulus is electrically 'shunted' diffusely within this CSF filled space. Researchers estimate that extradural stimulation results in the spinal cord receiving less than 10% of the delivered stimulus. The stimulus effect penetrates the spinal cord to a distance of 0.25 mm or less and the broad volumetric pattern encompasses both targeted (i.e. dorsal column) and non-targeted (i.e. dorsal rootlets) neural structures (He et al. 1994, Holsheimer 1998, Holsheimer 2002, Holsheimer et al. 2007).

The clinical importance of these limitations of the prior art are reflected in the numerous efforts made by device manufactures to mitigate the problems. These include the development of spatially distributed multi-contact extradural arrays and stimulation protocols that enable delivery of electrical charge distributions over widely variable anatomical patterns. This strategy allows the physician to adjust the anatomical location of maximal stimulation on the dural surface, but the presence of CSF shunting continues to markedly attenuate the stimulation effects within the spinal cord. Clinicians have also used a strategy of placing multiple cylindrical electrodes within the extradural space for the purpose of mechanically reducing the size of the CSF-filled space and displacing the electrode contacts to a position closer to the spinal cord (Holsheimer et al. 2007). A device modification recently introduced by one of the largest manufacturer of SCS devices seeks to address problems associated with movement of the spinal cord within the CSF-filled spinal canal that occurs when patients change position. These positional changes alter the spatial relationship between an extradural electrical source and the spinal cord, and the pattern of tissue activation. The new device senses patient position and automatically adjusts stimulus parameters for the purpose of achieving stable therapeutic effects. As with all other SCS design changes introduced to-date, the addition of a position sensor does not address the fundamental problem of CSF shunting of the electrical stimulus.

BRIEF SUMMARY OF THE INVENTION

The present invention addresses a major public health problem: medically intractable chronic pain. Specifically, embodiments of the invention provide devices and methods for providing effective symptomatic relief for patients suffering from chronic pain syndromes resulting from injury or disease affecting musculoskeletal, peripheral nerve, and other organ systems of the body. More specifically, embodiments of the invention provide surgically implanted devices adapted for electrical stimulation of tissues of the nervous system. Still more specifically, some exemplary embodiments of the present invention provide devices and methods for direct electrical stimulation of the spinal cord, optionally by wireless inductive coupling of signals from an electrical signal generator which may be located on the dura surrounding the spinal cord to an electrode assembly adapted to be implanted directly on the surface of the spinal cord, thus obviating the need for wires, leads or other such connections disposed through the dura. Many embodiments of the spinal cord stimulation devices described herein may be supported in engagement with the spinal cord by attaching features of the device to dentate ligaments extending laterally between the spinal cord and the surrounding dura, with either wireless or wired coupling to a signal generator disposed outside the dura. Most embodiments of the devices and methods of the present invention will electrically stimulate well defined, circumscribed sub-regions of the spinal cord with both a degree of spatial precision and a therapeutic level of electrical intensity that cannot be achieved using existing spinal cord stimulation (SCS) devices. In specific embodiments, the electrode assemblies comprise flexible electronic microcircuitry, optionally with thin-film electrode arrays, at least the latter of which are configured to be in direct physical contact with the surface of the spinal cord. The implanted electrode assemblies may be remotely powered and controlled (with no physical connections to or through the dural lining of the spinal canal), or may have a plurality of conductors extending through the dura, to selectively activate targeted regions of the spinal cord with extreme precision and the requisite electrical intensity.

The devices and methods of the subject invention address the most important deficiencies of current SCS devices in the prior art by incorporating the following design features into the device:

1) the electrical stimuli are delivered directly to the spinal cord;
2) a dense array of electrode contacts enables delivery of highly localized, spatio-temporally synchronized (could also multi-plex, alternating stimuli between various electrode montages), and positionally selective electrical stimuli to any targeted sub-region of the spinal cord;
3) the device does not mechanically tether or form a physical connection between the spinal cord and dura that significantly alters the natural support and flexibility provided by the dentate ligaments;
4) the implantable electrode assembly has an ultra-thin physical profile that does not obstruct or alter CSF flow patterns around the spinal cord;
5) the contact forces between the device and the spinal cord are stable and unvarying, and hence patient movement does not affect these contact properties, which results in optimal electrical coupling between electrode contacts and spinal cord tissue;
6) the compliant nature of the device materials accommodates pulsations of the spinal cord without any harmful reactive or dissipative counter-forces;
7) the materials used to construct the device are highly resistant to electronic or structural failure with break rates that may be lower than (or similar to) existing devices, optionally using materials that are already included in stimulation implant devices or novel proprietary materials;
8) the surgical procedure (laminectomy) used to implant the device is well established and safe, and when performed by skilled practitioners, the risk of CSF fistula formation with this procedure will not differ significantly from complication rates associated with current surgical implantation procedures used to implant extradural electrode arrays;
9) the increased duration of implantation surgery, compared to current procedure times for surgical implantation of extradural SCS devices, will not exceed 30 minutes; and
10) the manufacturing cost of the new device may (in at least some embodiments) be less than that for existing devices (particularly for the 'wired' I-Patch).

The electrode assembly, hereinafter referred to as the Iowa-Patch (I-Patch) fulfills at least some of these design criteria, and is composed of advanced flexible electronics technologies. The electronic elements of the I-Patch are imbedded in (optionally being between layers of) a flexible polymeric or elastomeric "patch" or substrate. Electrical stimuli are delivered via an array of contacts that, when in position, can provide axial and circumferential coverage directly onto the lateral and/or dorsal surfaces of the spinal cord. Precisely localized patterns of spinal cord stimuli are achieved by selectively activating the preferred combinations of electrode contacts in any desired, programmable spatio-temporal sequences. In one embodiment, flexible polymer 'arms' of the device are optionally contoured to provide a continuous, gentle inward "capture" force that insures an optimal electrical interface between the device contacts and spinal cord tissue, while avoiding mechanical constriction of the spinal cord.

In one embodiment, the dorsal (outer) surface of the I-Patch contains embedded microcircuitry that implements stimulus delivery algorithms. Circuit elements may include an RF antenna that receives power and control commands from an intra- or extradural device described below, as well as other circuit elements that generate and route electrical stimuli to the appropriate electrode contacts. The self-contained I-Patch may have no mechanical or other physical connection with any other element of the SCS system. Alternatively, small gauge, flexible conductors may extend between the dura and the spinal cord along a dentate ligament, to which said conductors may be affixed, said ligaments being the structures of the body that support the spinal cord within the dura. Hence, when the device is in place there is no substantive spinal cord tethering or disruption of CSF flow dynamics around the spinal cord. All the device surfaces, with the exception of the electrode contacts, are either composed of or coated with a biocompatible insulating material, such as medical grade silicone, and the finished intradural device is very thin, on the order of (and typically being) 0.5 mm or less.

In one embodiment, the I-Patch is inserted surgically by performing a laminectomy, creating a mid-line dorsal durotomy, inserting the device onto the spinal cord, and then suturing the dura closed. Because, after implantation of some embodiments, no portion of the device penetrates the dura, and the dura is opened and closed in an optimally controlled manner, the risk of CSF fistula formation will be low.

A power and control signal transfer circuit assembly, constructed within a thin, hermetic encapsulation, is positioned either in the extradural space (over an exterior surface of the dura) or on the inside surface of the dural membrane, in either case overlying the I-Patch implant. This transfer circuit assembly generates power and command signals that are transmitted across the CSF filled space surrounding the spinal cord, and are received by the I-Patch, either wirelessly or along a conductor. The power and/or signal circuit assembly (or components thereof) may be incorporated in the main power supply battery and control circuit assembly in wired embodiments of the I-Patch. The extradural device is secured in place using sutures and includes flexible electrical leads that are connected to a power supply battery and control circuit assembly that is implanted in the subcutaneous tissue of the patient's abdominal wall. The entire system can be controlled via wireless commands that employ technologies similar to those used in standard SCS devices. The flexible microelectronics materials used are extremely robust and resistant to breakage. Such circuits have been used extensively in harsh conditions ranging from deep space (rockets and satellites) to consumer use of folding hand-held cell phones.

The I-Patch system specifically targets one aspect of SCS device performance and value: treatment efficacy. Because of improvements in the ability to precisely activate targeted sub-regions of the spinal cord, the I-Patch system will significantly improve the treatment efficacy when compared to current devices.

The I-Patch system can be used for all spinal cord stimulation applications, including treatment of patients with Parkinson's disease, Spinal Cord Injury, and Congestive Heart Failure. While usually employing surface contact electrodes, the system can also be modified to incorporate penetrating microelectrodes that emanate from the I-Patch platform and enable delivery of electrical stimuli to sub-surface neural targets. Such a system can be used not only in the spinal cord, but also in the brain and other organ systems.

One skilled in the art can see that many other embodiments of means and methods for non-contact spinal cord stimulation according to the technique of the invention, and other details of construction and use thereof, constitute non-inventive variations of the novel and insightful conceptual means, system, and technique which underlie the present invention.

Thus, in a first specific aspect of the present invention a method for treating pain in a patient comprises conformably positioning an electrode array over a surface of the patient's spinal cord so that a plurality of individual electrodes in the array directly contact selected locations on the spinal cord. Electrical stimulation energy is then delivered in a controlled spatio-temporal sequence to a targeted sub-region of the spinal cord to relieve pain without stimulating dorsal nerve rootlets. Typically, conformably positioning the electrode array comprises circumscribing a structure of the array around the spinal cord, with some embodiments circumscribing more than 180° but less than all (360°) of the spinal cord circumference. Conveniently, the circumscribing array structure can have an elastic C-shaped geometry which can be opened and elastically closed over the spinal cord to hold the electrode array in place while accommodating spinal cord pulsation and other motions. In this way, the electrode array structure when implanted to circumscribe the spinal cord will not substantially obstruct CSF flow, thus reducing the risk of syrinx formation. Alternative embodiments may circumscribe less than 180° of the spinal cord, with the electrodes of the array optionally being disposed primarily or even entirely over the dorsal surface of the spinal cord between left and right dentate ligaments.

In preferred aspects of the method of the present invention, the individual electrodes will be distributed over at least points on the dorsal surfaces of the spinal cord, and optionally over the lateral and ventral surfaces, so that sufficient regions of the spinal cord surface are contacted to permit selective actuation of the electrodes and targeted stimulation of a variety of spinal cord anatomical sites as described in more detail below. As described above, stimulation of the implanted electrode structure on the spinal cord will optionally be achieved by wirelessly transmitting energy to the electrode array from a signal generator disposed remotely from the array. Usually, the signal generator will be implanted to lie either directly on the external surface of the dura or just underneath the internal surface of the dura, preferably directly over the implanted location of the spinal cord electrode array. Alternatively, however, the signal generator in some cases could be more remotely located and provide for transcutaneous or other remote transmission of power and signal to the implanted spinal cord electrode array. Embodiments may include one or more flexible conductors (such as a flex-circuit, conductor wires, or conductor cables) extending between the array structure and an implanted generator system, with the conductors traversing through the dura and often extending along and being affixed to a dentate ligament.

In still further aspects of the present invention, an electrode array adapted to conform to an exterior surface of a patient's spinal cord comprises a compliant backing having an interior surface and an exterior surface, where the interior surface is adapted to lie in contact directly over the exterior surface of the spinal cord. A plurality of electrodes are formed over at least a portion of the interior surface, and transceiver and control circuits are disposed on or immediately beneath the exterior surface of the compliant backing. The transceiver's antenna may be adapted to receive power and signals from a remote signal generator, as described above, while the circuitry will be able to accept and process power and information signals from the antenna and convert the resulting currents to nerve stimulating pulses to be delivered by the electrodes to the spinal cord. The electrode array may include a C-clamp structure adapted to resiliently circumscribe at least a portion of the spinal cord, preferably circumscribing over 180° of the circumference while not completely enclosing the entire circumference.

In some preferred embodiments, the electrode circuitry carried by the electrode array will be adapted to selectively stimulate individual electrodes in response to the external signals received by the transceiver's antenna in order to deliver spatio-temporally selected stimuli to targeted regions of the spinal cord. Hence, a signal generator or other external circuitry may be programmed to treat particular conditions by stimulating targeted regions of the spinal cord, and such targeted stimulation will be achieved by selectively energizing particular ones of the individual electrodes which are part of the electrode array. Preferred anatomical target regions within the spinal cord will be chosen by the neurosurgeon and consulting neurologists and might include the thoracic, lumbar and sacral regions.

BRIEF DESCRIPTION OF THE DRAWINGS

FIGS. 14, 15, and 15A illustrate spiral and staggered electrode patch variations according to the present invention.

DETAILED DESCRIPTION OF THE INVENTION

Figure 1:
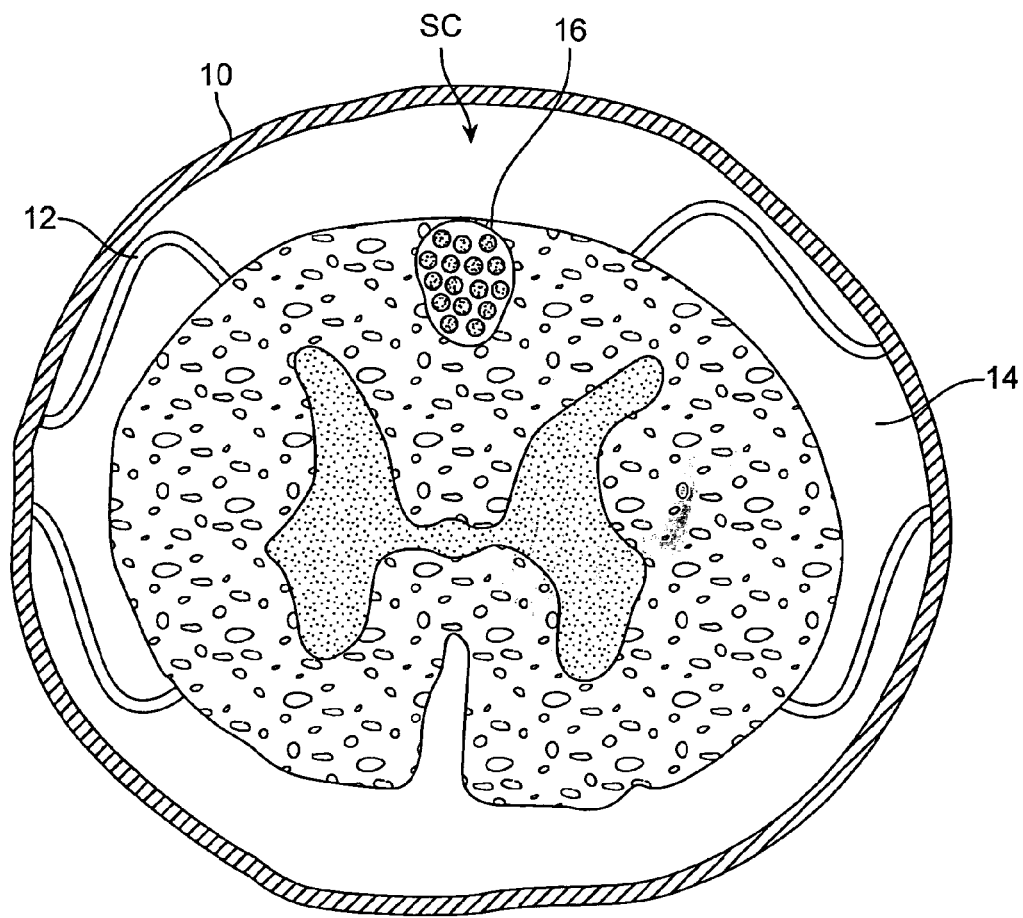
FIG. 1 shows a cross-sectional diagram of selected anatomical elements of the spinal cord.

FIG. 1 shows a cross-sectional diagram of selected anatomical elements of the spinal cord. These include the layer of dura mater 10 that encompasses the spinal cord SC and encloses the spinal canal, the dorsal nerve rootlets 12, the zone of cerebrospinal fluid 14 that separates the outer surface of the spinal cord from the inner surface of the dura, and the axons 16 that would be targeted by spinal cord stimulation instrumentation.

Figure 1A:
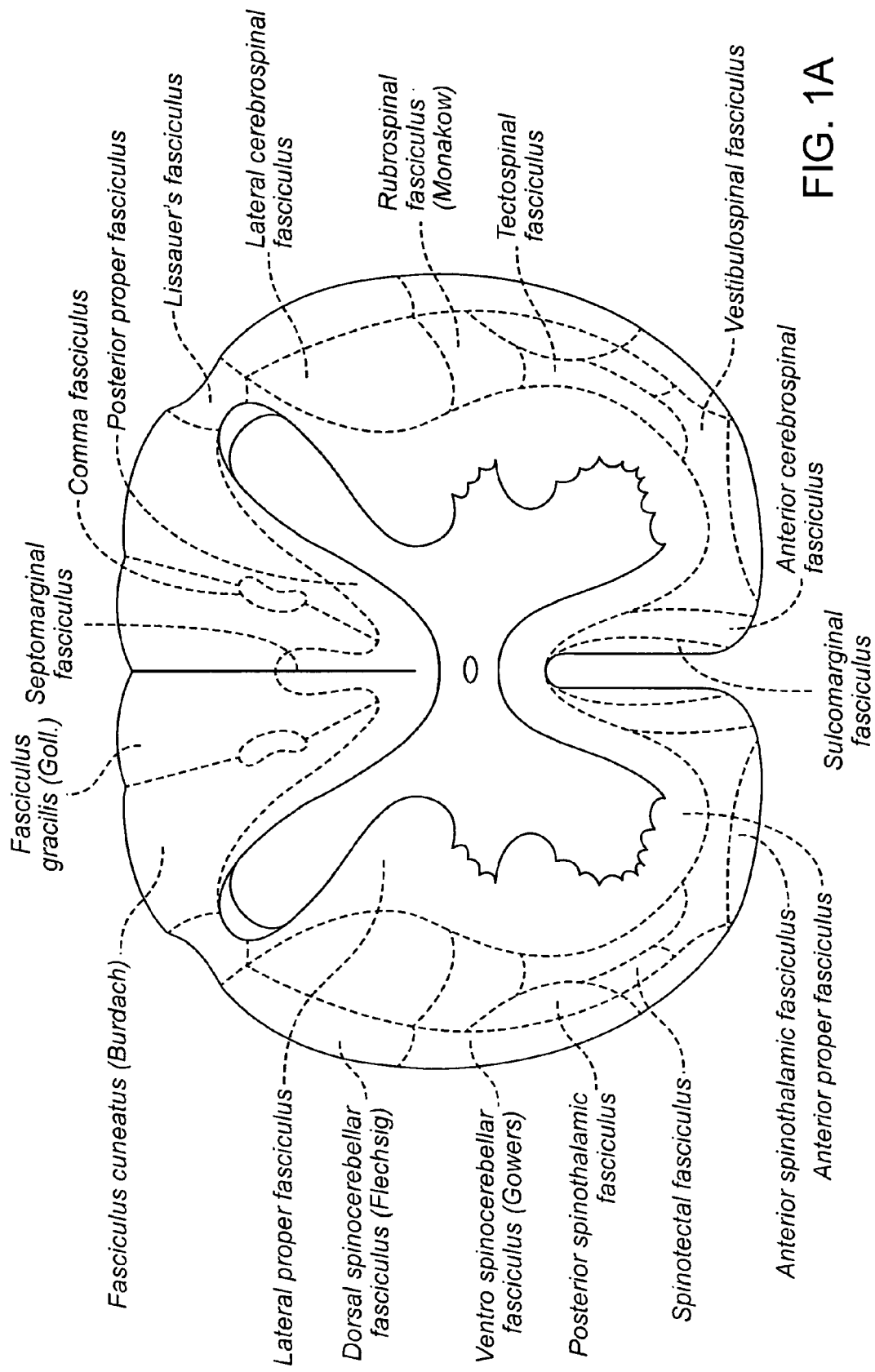
FIG. 1A shows a cross-sectional view of the spinal cord with specific anatomical locations identified.

FIG. 1A illustrates the complex anatomical arrangement of the postulated human spinal cord pathways. In the large dorsal column pathways (*f. gracilis, f. cuneatus*) activation of large numbers of axons that are located greater than 0.5 mm deep below pial surface will likely result in broader somatotopic coverage of painful areas of the body and an increased magnitude of pain attenuation effects. Activation of axons within deeply positioned dorsal mid-line structures (e.g. septomarginal f., posterior proper f.) may result in complete relief of visceral pain. Pathways positioned within the lateral and anterior regions of the spinal cord are not activated by current SCS devices. There are many potential stimulation targets in these regions, including the posterior and anterior spinothalamic tracts which conduct pain and temperature signals to the brain.

Spinal cord stimulation may also be effective in treating patients with movement disorders (e.g. Parkinson's Disease). There are a large number of potential motor and motor-modulation pathways throughout the human spinal cord that may represent optimal targets for this novel clinical application, e.g. lateral cerebrospinal f., rubrospinal f., tectospinal f, dorsal spinocerebellar f., ventro spinocerebellar f., all of which are beyond the range of current SCS devices. The I-Patch system (surface and penetrating electrode variants) will be capable of selectively activating any spinal cord pathway, in any location, in a patient with a functionally intact spinal cord. Stimulation of these sites will likely result in markedly improved spinal cord stimulation clinical efficacy.

Figure 2:
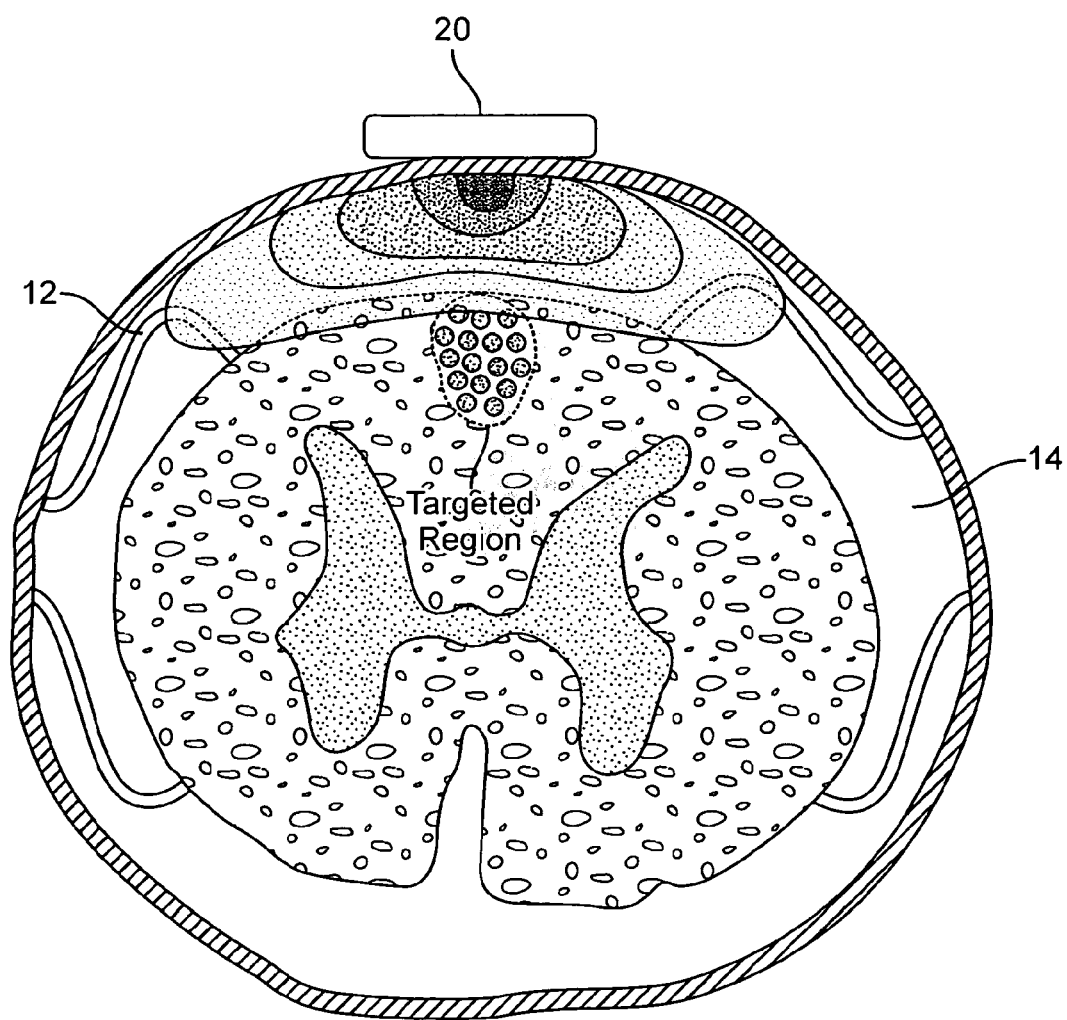
FIG. 2 shows a cross-sectional diagram of the results of extradural stimulation of the spinal cord.

FIG. 2 shows a cross-sectional diagram of the results of extradural stimulation of the spinal cord. The standard epidural stimulating electrode 20 is placed on the outside of the dura, and the field it produces is attenuated significantly by the presence of the CSF 14. The resulting field within the spinal cord is very weak, having little effect on the targeted dorsal column axons, but instead causing discomfort for the patient via parasitic activation of the dorsal rootlets 12.

Figure 3:
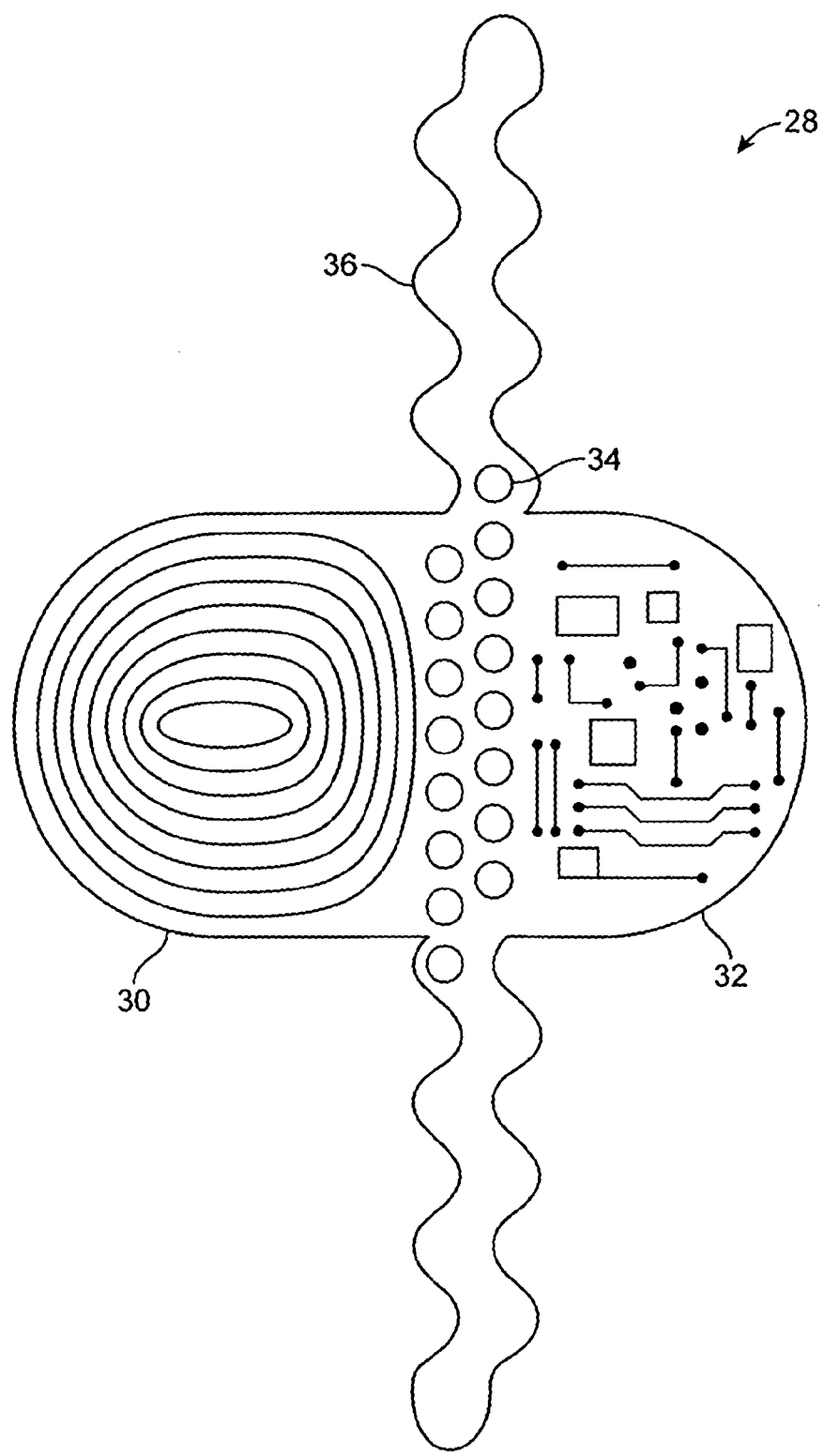
FIG. 3 shows an illustration of the principal electronic subsystems resident on a wireless embodiment of the I-Patch receiver element or array structure.

FIG. 3 shows a conceptual illustration of the principal electronic subsystems resident on a wireless embodiment of the I-Patch receiver or array structure element 28. Seen there (on the left) are the turns of a microfabricated coil 30 that is configured to serve as an RF receiver that couples inductively to the counterpart coil on a paired transmitter element, this enabling the I-Patch to receive power, information, and control signals. Also shown (on the right) are the circuits 32 constituting the control elements that regulate the size, timing and distribution of the stimuli that act on the electrodes 34 (center). Flexible attachment arms 36 extend from either side of a central body of the I-Patch, with the attachment arms typically being formed at least in part of the substrate or backing material on which circuit components 32 are mounted or formed.

Figure 4:
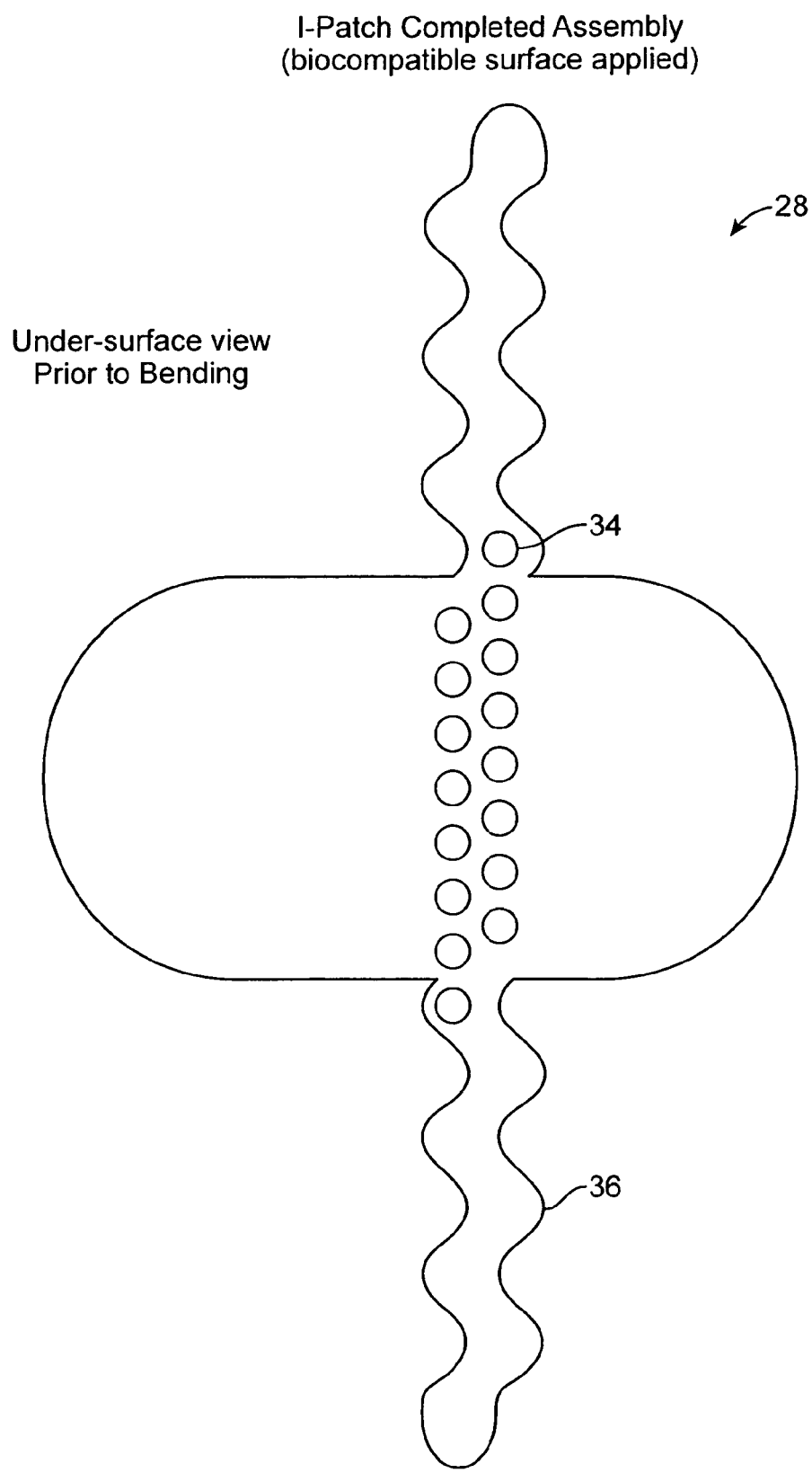
FIG. 4 shows an illustration of the underside of the I-Patch receiver element of FIG. 3, which would be in contact with the surface of the spinal cord.

FIG. 4 shows an illustration of the underside of the I-Patch receiver element, which would be in contact with the surface of the spinal cord. The electrodes 34 (center) are positioned by the neurosurgeon over the region of spinal cord to be stimulated. The underside of the biocompatible I-Patch is in contact with the surface of the spinal cord, and held to it by the gentle clamping action of the extension arms 36 shown in the figure.

Figure 5:
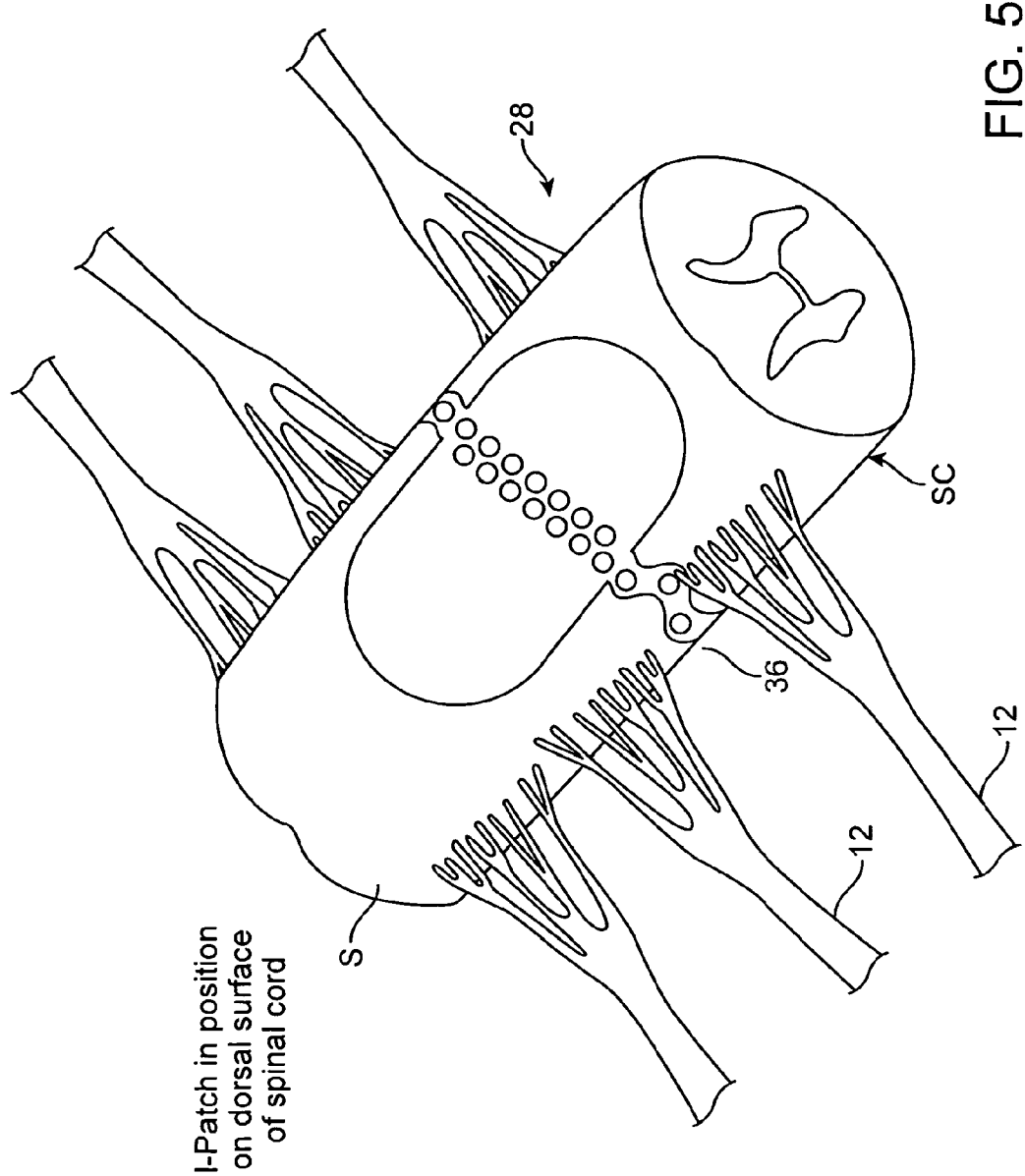
FIG. 5 shows the deployment of the I-Patch receiver device on the surface of the spinal cord.

FIG. 5 shows the deployment of the I-Patch receiver device 28 on the surface of the spinal cord SC. The extension arms 36 of the receiver device 28 partially encircle the body of the spinal cord SC, thus gently clamping the I-Patch to it. The extension arms are positioned to reside between the dorsal rootlets 12, and not be in contact with them. Under some circumstances a number of dorsal rootlets may be sectioned to accommodate placement of the I-Patch.

Figure 6:
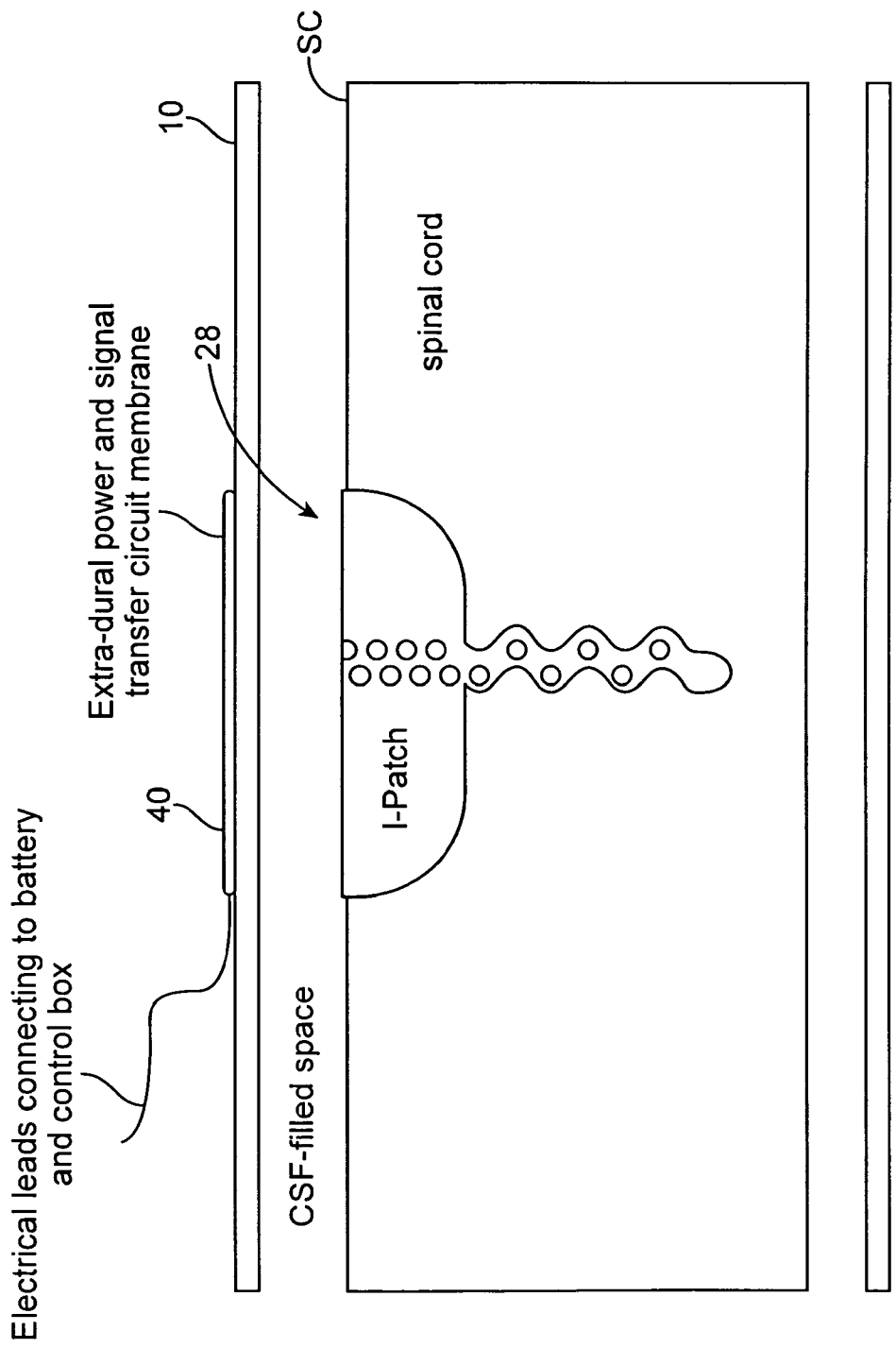
FIG. 6 shows a lateral view of the relative positions of the wireless I-Patch transmitter and receiver devices, on the surfaces of the dura and spinal cord, respectively.

FIG. 6 shows a lateral view of the relative positions of the I-Patch transmitter 40 and receiver 28 devices, on the surfaces of the dura 10 and spinal cord SC, respectively. The transmitter 40 and receiver 28 patches are inductively coupled to each other by electromagnetic fields established through current flows in the windings on their respective surfaces. The strength of the coupling can be adjusted by regulation of the strength of the current flow. In this way, power, information, and control signals can span the zone of CSF resident between the inside surface of the dura and the outer surface of the spinal cord.

Figure 7:
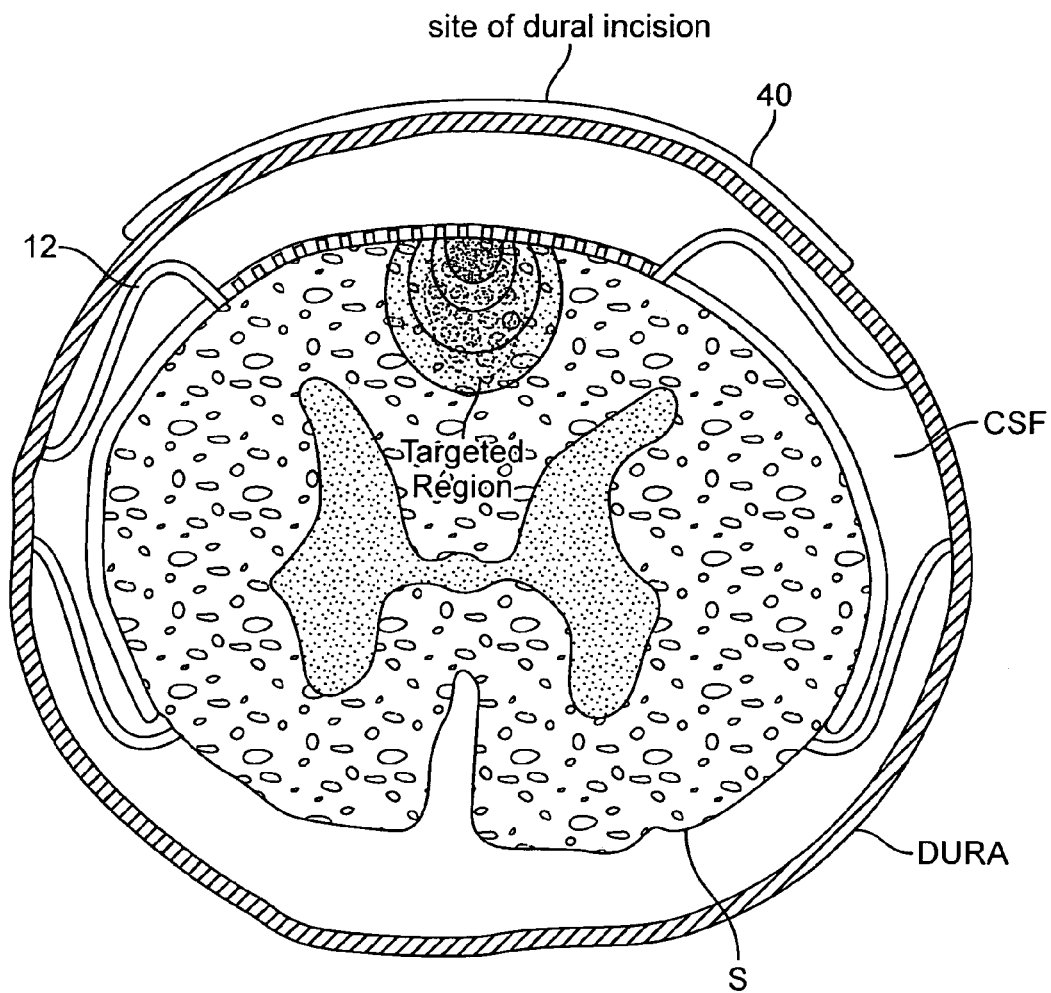
FIG. 7 shows a cross-sectional view of the relative positions of the I-Patch transmitter and receiver devices, on the surfaces of the dura and spinal cord, respectively.

FIG. 7 shows a cross-sectional view of the relative positions of the I-Patch transmitter 40 and receiver 28 devices, on the surface of the dura 10 and surface S of the spinal cord SC, respectively. By positioning the very thin I-Patch receiver directly on the surface S of the spinal cord SC, it is possible to drive the electrodes such that the stimuli fields penetrate through the whole treatment zone of interest and are not attenuated by the CSF. Also, this type of stimulus field concentration insures that there is no parasitic excitation of the dorsal rootlets, with the resulting associated pain. To a rough approximation, the instantaneous electric field, E, within the stimulation zone will be given by $E=\sigma/2\kappa\in_0$ where $\sigma$ is the surface charge density created at the electrode's surface, $\kappa\in_0$ is the product of the dielectric constant of the spinal cord substrate and the permittivity of free space. End effects associated with the geometry of each individual stimulus electrode will modify this simple model, as will superposition of the fields due to the simultaneous activation of one or more neighboring electrodes.

Figure 8:
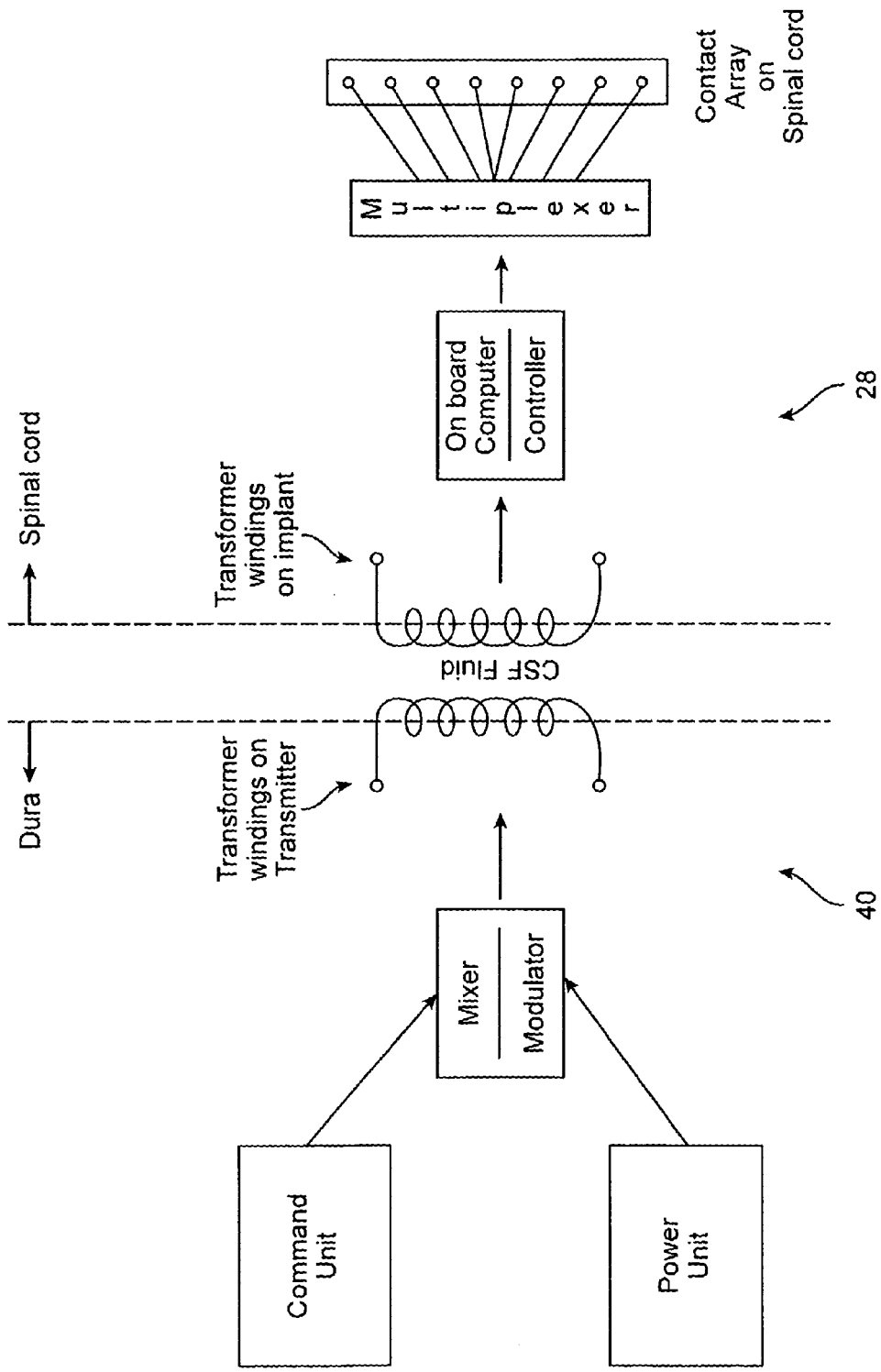
FIG. 8 shows a schematic representation of the inductive coupling action taking place between the I-Patch transmitter and receiver devices.

FIG. 8 shows a schematic representation of the inductive coupling action taking place between the I-Patch transmitter 40 and receiver 28 devices. As seen there, the power, information, and control signals generated by the transmitter device on the dura side of the system are inductively coupled across the CSF fluid to the receiver device, where they are operated on by the on-board controller, and stimuli signals are distributed to the electrodes. The inductive coupling action is governed by the mutual inductance between the two sets of windings.

The optional 'wireless' design of the I-Patch system is a very important design aspect of some embodiments. However, alternative embodiments employ 'wired' versions of I-Patch devices that are safe and effective, as described below. Embodiments of these wired devices may have higher rates of mechanical failure and be associated with increased risks of complications compared to a wireless I-Patch version, but would function and potentially be useful for certain applications.

The I-Patch can deliver electrical stimuli to regions of the spinal cord that are targeted by current SCS devices. This is accomplished by positioning electrodes on the pial surface of the spinal cord. It is highly likely that therapeutic effects can also be achieved by selectively stimulating circumscribed sub-regions of the spinal cord positioned deep to the pial surface. In fact, the spatio-temporally selected electrical stimulation of certain structures within the central regions of the spinal cord may result in therapeutic benefits that cannot be achieved with surface stimulation. A broad range of clinical applications, beyond the currently targeted chronic pain treatments, will likely be available via placement of chronic penetrating I-Patch electrodes (e.g. activation of motor pathways to treat patients with movement disorders or paralysis).

Figure 9:
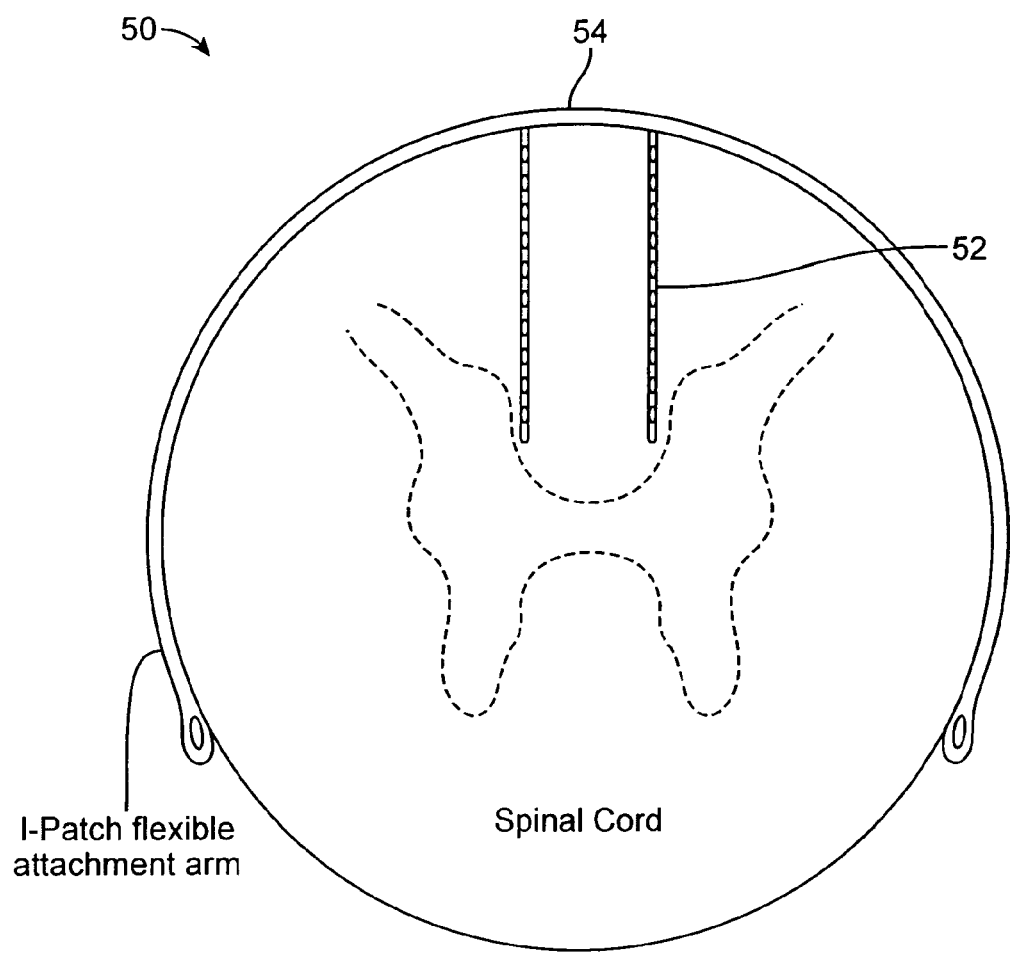
FIG. 9 illustrates a I-Patch having penetrating electrodes for accessing internal target regions within the spinal cord.

The penetrating electrode I-Patch 50 is illustrated in FIG. 9. Multi-contact penetrating electrodes 52 extend from the I-Patch main assembly 54. The interface between the main assembly and penetrating electrode shaft may be held rigid (at least during implantation), allowing the surgeon to insert the penetrating electrode into the spinal cord by advancing the I-Patch device toward the dorsal spinal cord surface using the I-Patch Applier. Once the main assembly is in contact with the surface of the spinal cord, the flexible I-Patch attachment arms are optionally released resulting in a stable attachment between the spinal cord and the electrode assembly. In some embodiments, the electrodes may, after implantation, be supported relative to each other and the substrate or backing of the I-Patch with resiliently flexible materials, thereby allowing the overall array of electrodes to accommodate pulsation and the like. Suitable resilient flexible support of the electrodes may be provided using a flexible material spanning between the electrode and walls of an aperture through the substrate, with the flexible material optionally comprising a separate layer bonded to the substrate, material insert molded within apertures through the substrate, or the like. Electrical stimuli are delivered through select penetrating electrode contacts using control circuitry embedded in the I-Patch main assembly. The geometric contour of electrical stimulation effects surrounding a given penetrating electrode contact is shaped by the selection of other I-Patch surface and penetrating electrode contacts that are incorporated into bi-polar, or multi-polar stimulation montages.

Figure 10:
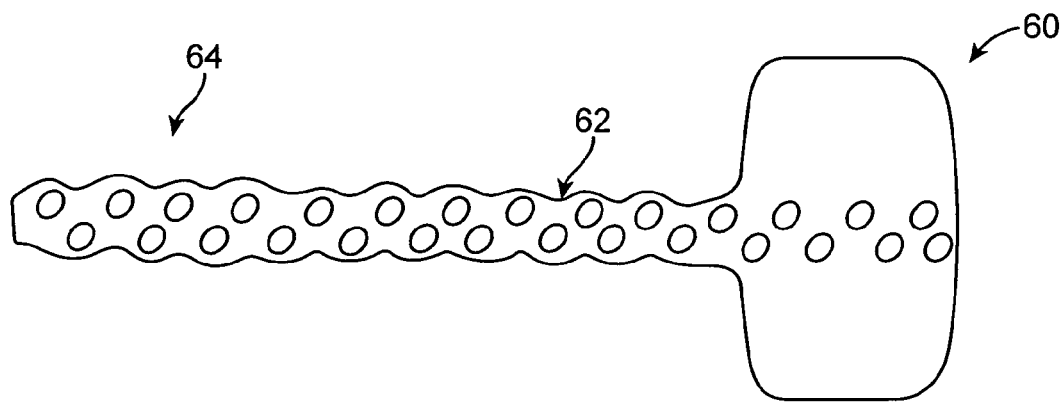
FIGS. 10-13 illustrate a full-circumference pliable electrode structure and method of implantation, intended to fully circumscribe the spinal cord to provide access to additional targeted regions therein.
Figure 10A:
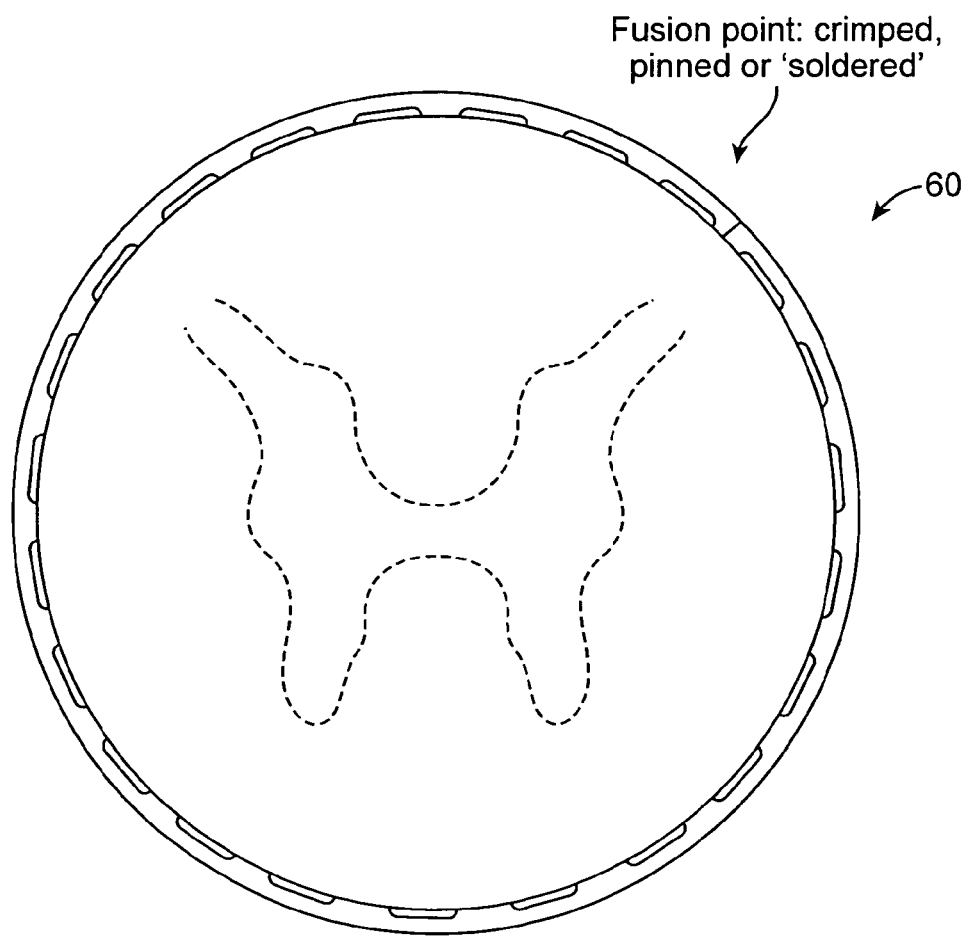

Clinical applications that target neural pathways on ventrally located surface structures of the spinal cord that may be targeted with a malleable full-circumference I-Patch prototype as illustrated in FIG. 10.

Figure 11:
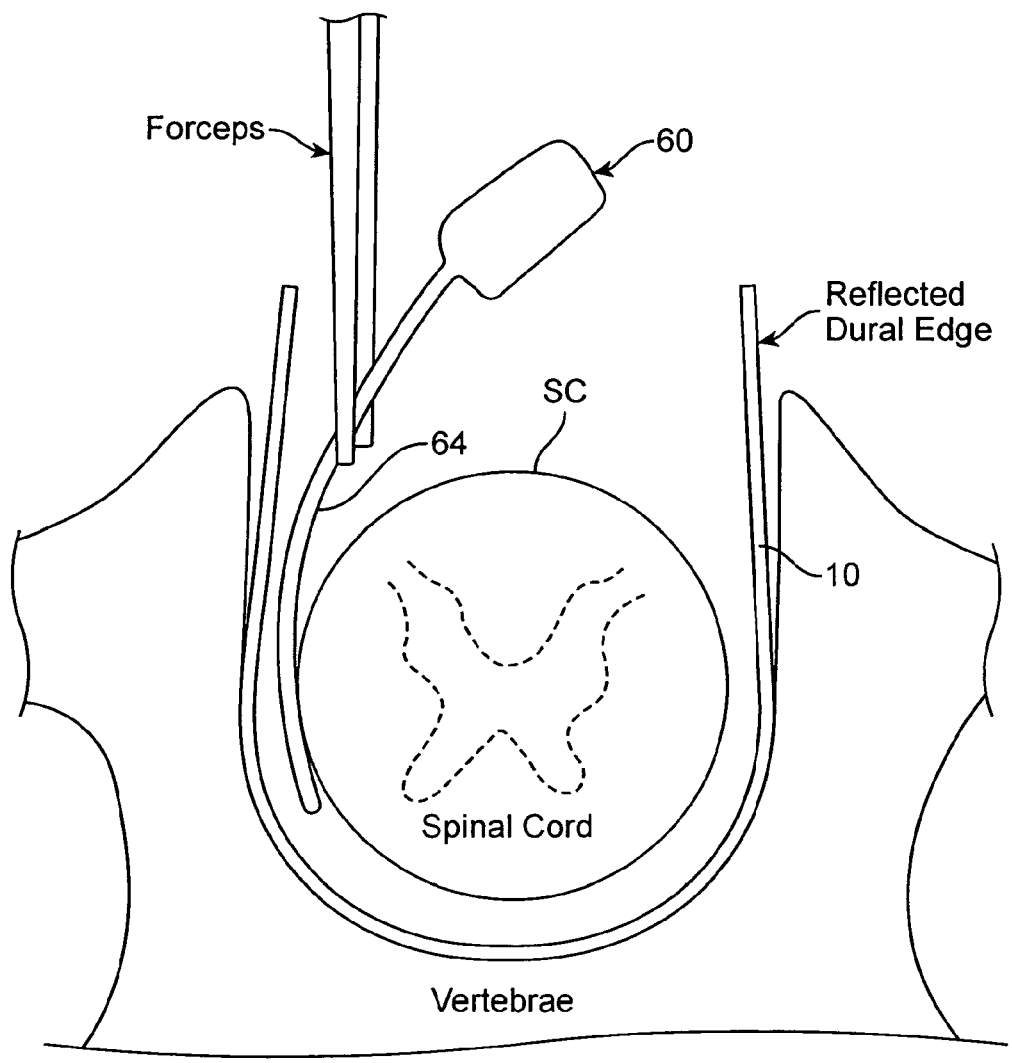
Figure 12:
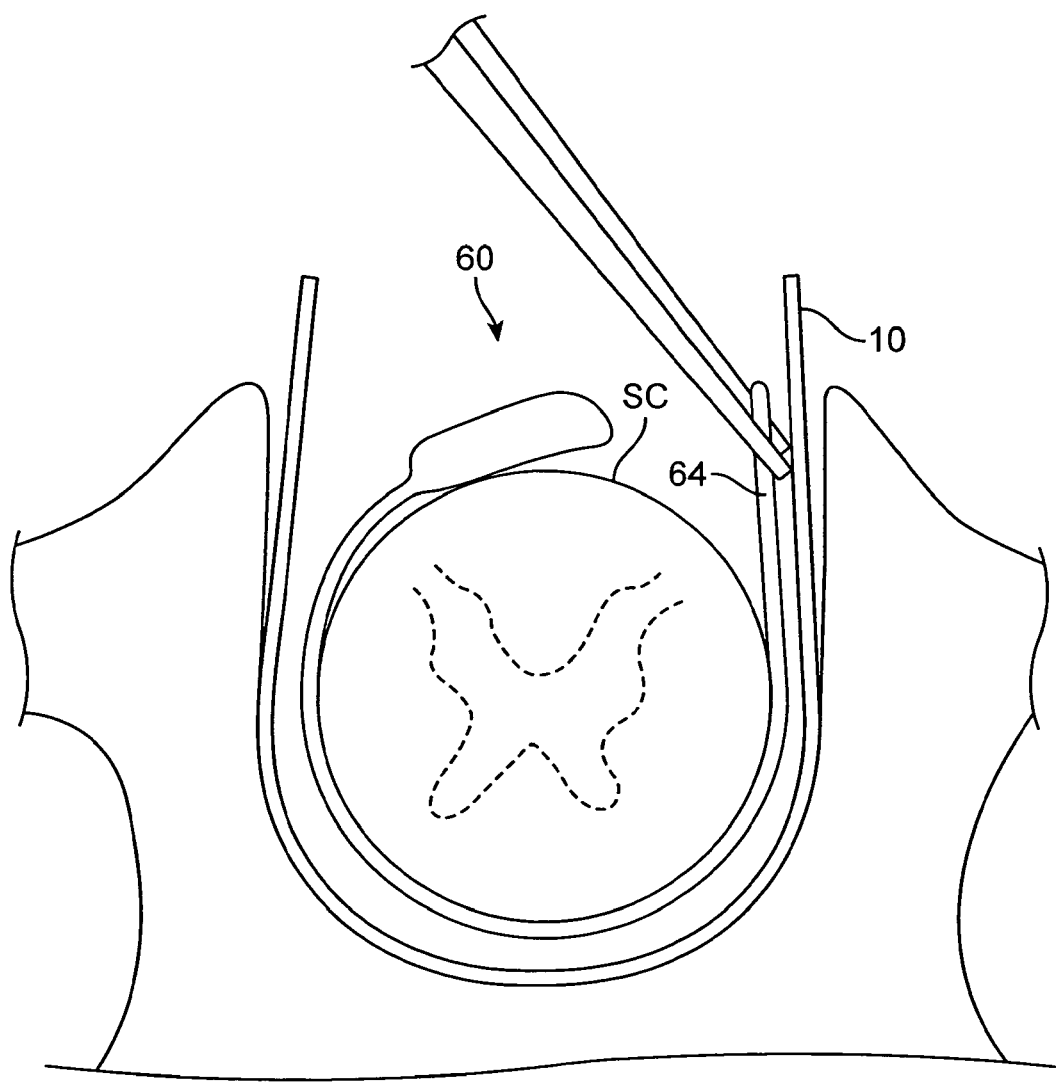
Figure 13:
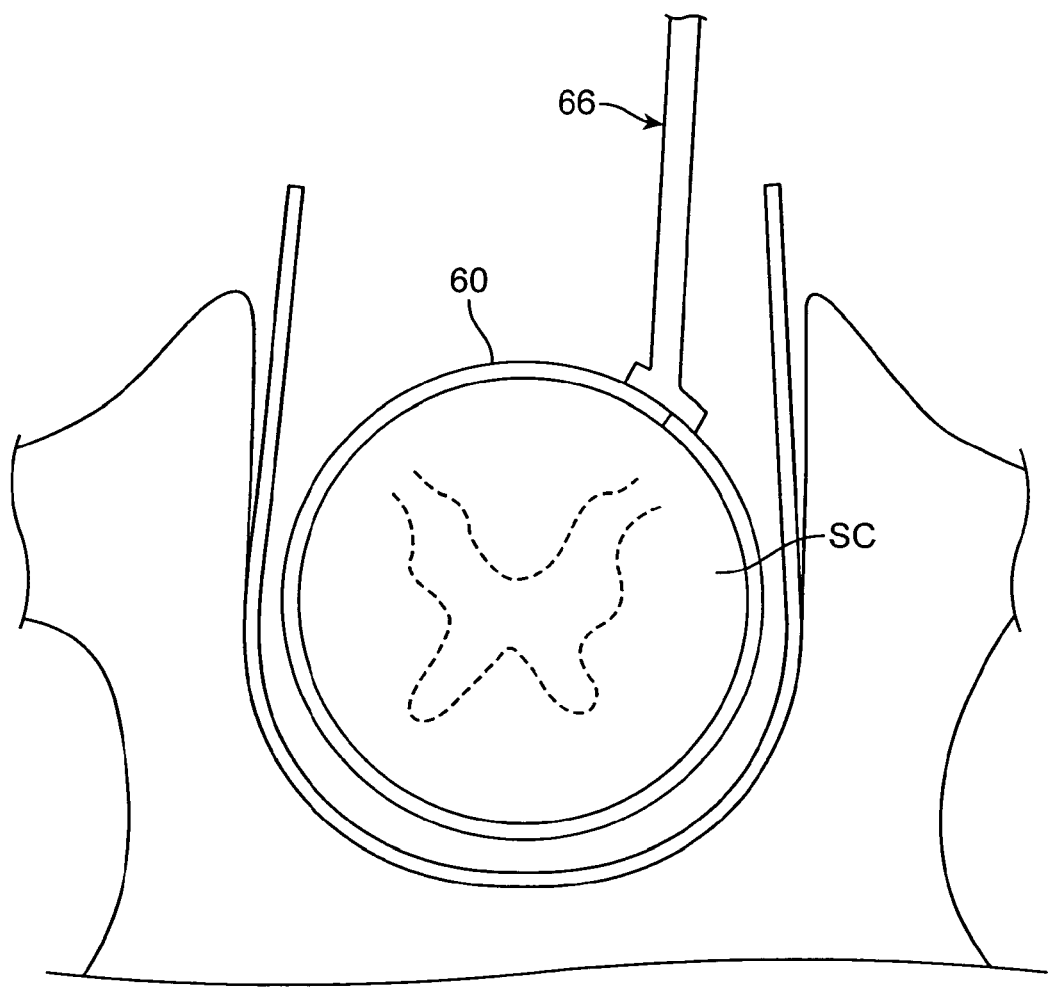

In contrast to the I-Patch designs with elastic C-clamps, as described above, the device 60 of FIG. 10 is fully pliable and has no 'memory' of the curvature of the spinal cord. A dense array of electrode contacts 62 is imbedded in a flexible band 64 extending from a body of the device and capable of fully circumscribing the spinal cord. This flexible band 64 is inserted in the space between the dura and the spinal cord and gently advanced until the leading edge is visible on the opposite side of the spinal cord (FIGS. 11 and 12). The leading edge of the electrode band is then crimped, pinned or otherwise secured to the main assembly of the I-Patch device (FIG. 13) by a crimping device 66 or the like.

The pliable band achieves the objective of positioning electrode contacts in an uninterrupted linear array covering the entire circumference of the spinal cord. The drawbacks of this design are that the insertion technique is more difficult and associated with increased risks compared to the standard I-Patch. When advancing the electrode band around the circumference of the spinal cord there will be a small risk of injuring nerve roots or causing a hemorrhage. Also, the mechanical contact, and thus electrical coupling, achieved between the electrodes and spinal cord surface will be less optimal than with the standard I-Patch prototype. The full-circumference band cannot be attached so tightly that it impedes spinal cord pulsation; this would result in injury to the neural tissue. Conversely, a 'loose fitting' circumferential band will not exert the optimal inward forces on the electrode contact and thus allow spinal fluid to flow between the electrode contact and the pial surface resulting in sub-optimal electrical coupling. One potential design variant would involve having the electrode contacts protrude from the flexible band, allowing for firm contact between electrodes and the pial surface, but also gaps between the pial surface and the non-electrode bearing portions of the flexible arm. These gaps would accommodate pulsatile spinal cord expansion and contraction.

Figure 14:
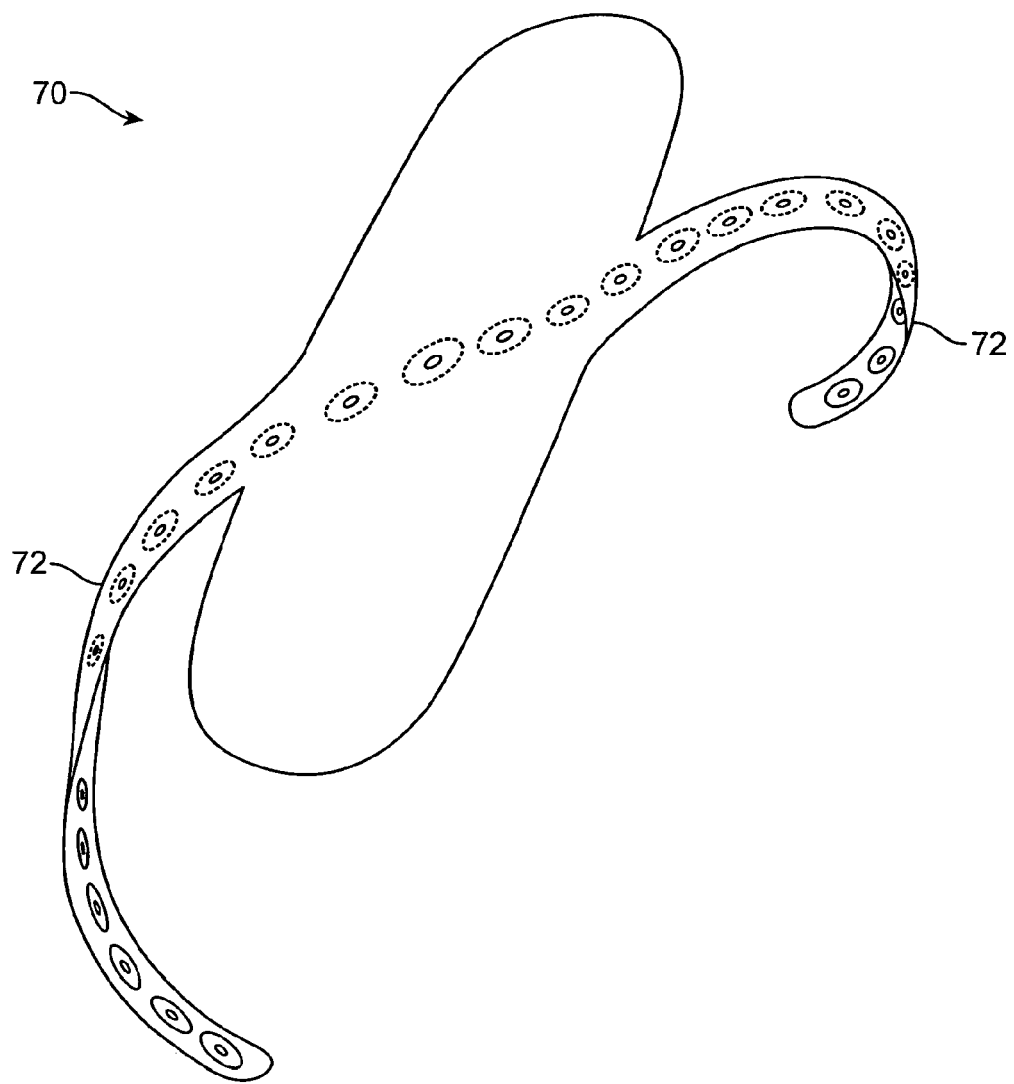
Figure 15:
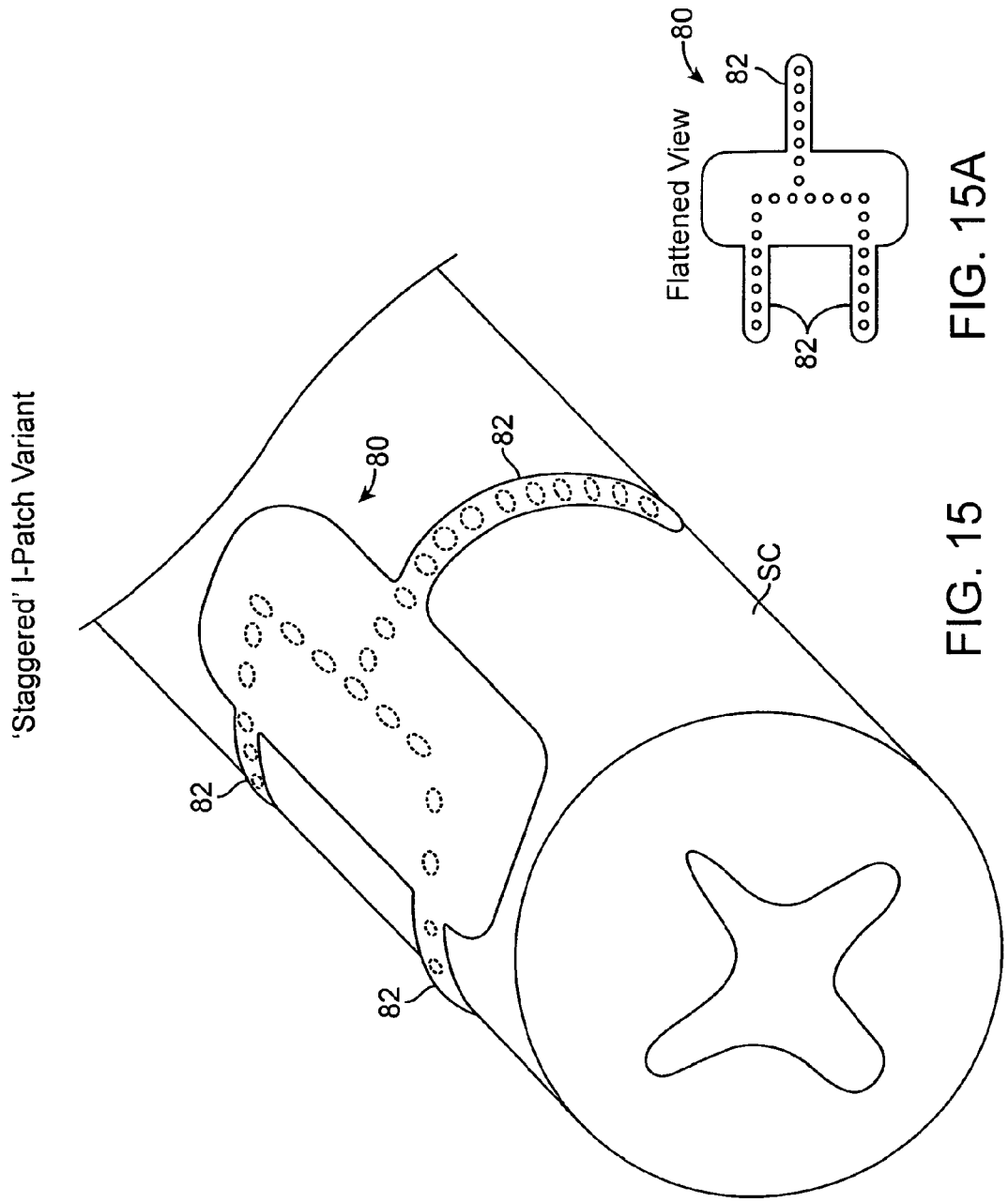

Alternative patch designs with reduced spinal cord compression and improved accommodation of spinal cord pulsations are illustrated in FIGS. 14 and 15. The devices of FIGS. 14, 15, and 15A have incomplete ring configuration and elastic properties that enable the devices to gently expand and contract along with the spinal cord. The I-Patch variant 70 of FIG. 14 has spiral attachment arms 72, and the staggered I Patch variant 80 of FIGS. 15 and 15A has staggered arms 82

The devices of FIGS. 14 and 15 further reduce the degree of mechanical constriction in a given cross-sectional portion of the spinal cord. The net effect of gently exerting inward forces on the device to maintain contact with the spinal cord is achieved by 'staggering' the attachment arms, or by using 'spiral' configured attachment arms.

Figure 16:
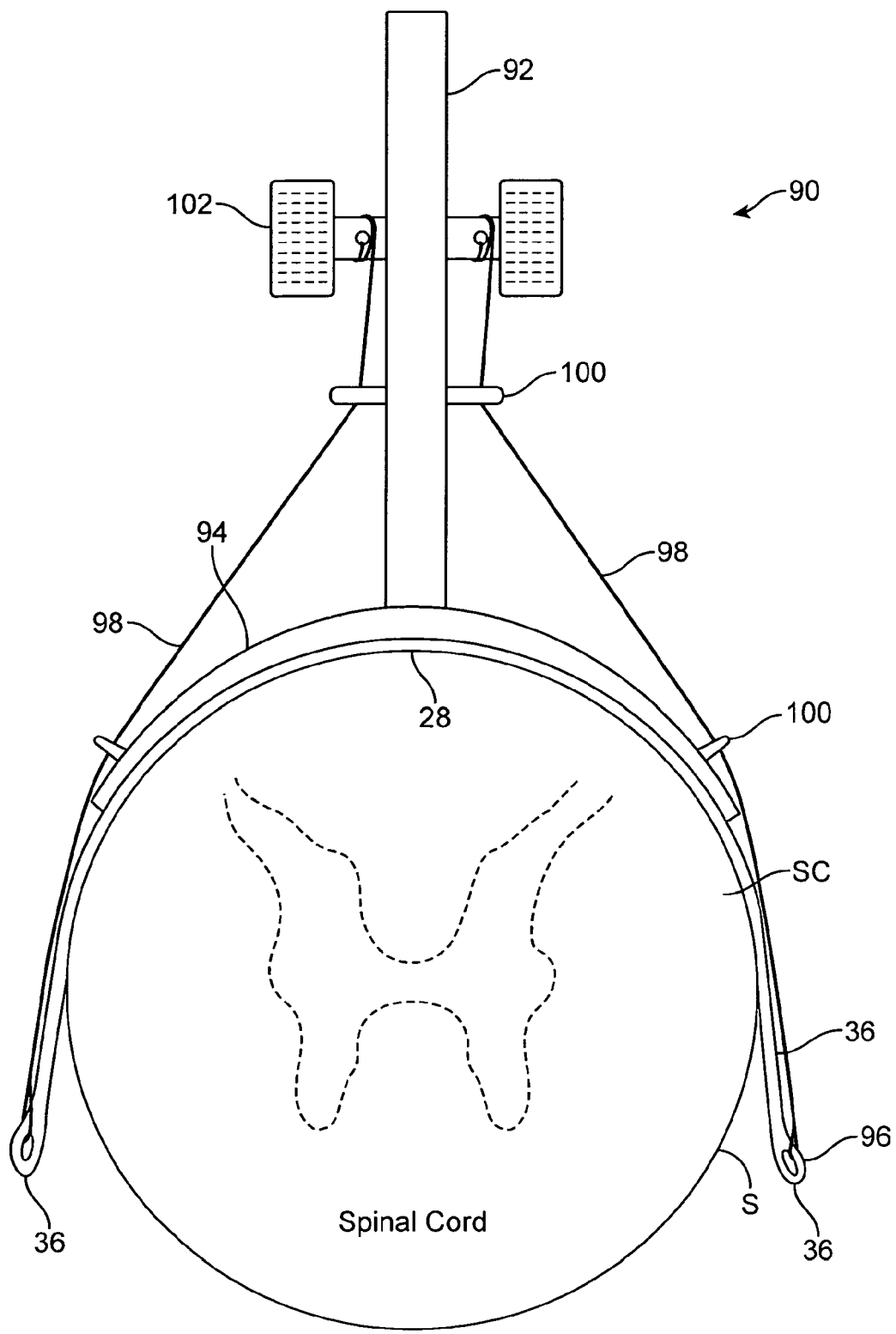
FIGS. 16 and 17 illustrate an insertion device for implanting the electrode assembly of the present invention on a spinal cord.
Figure 17:
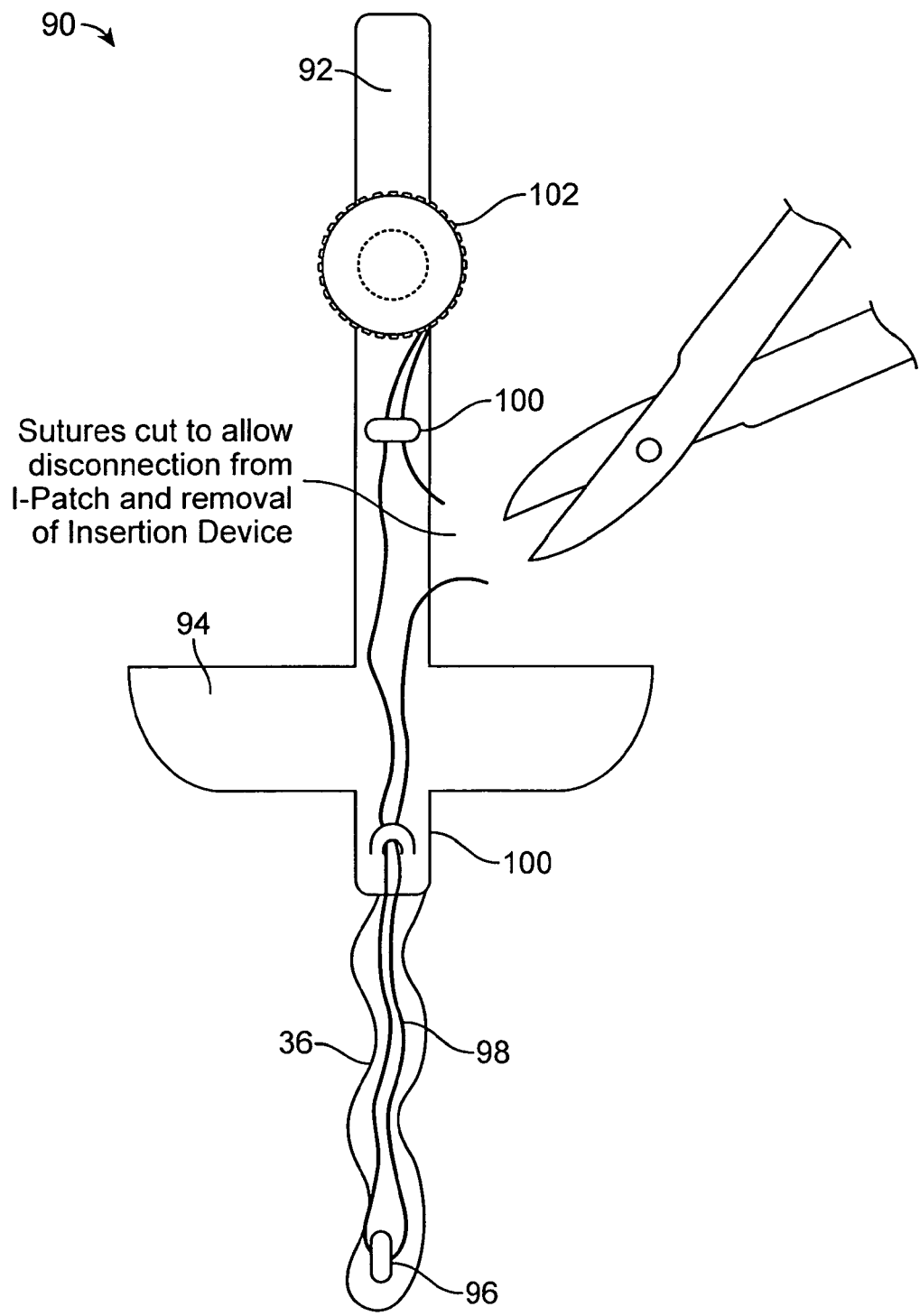
Figure 18:
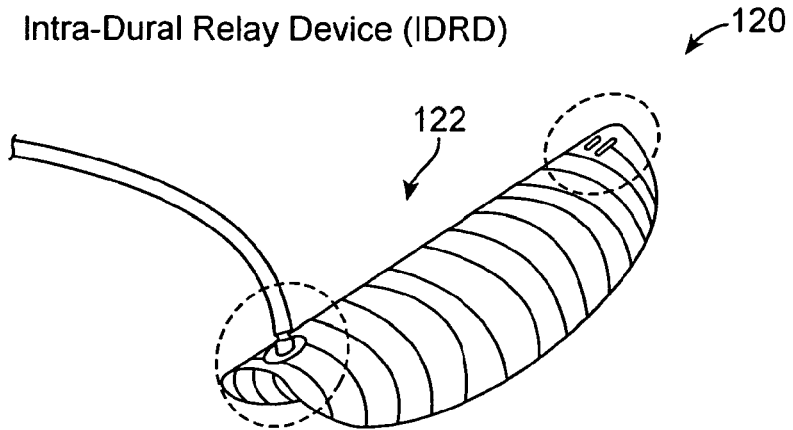
FIGS. 18 through 21 illustrate an intra-dural relay device for delivering power and signals to the implanted I-Patch when implanted on the spinal cord.
Figure 18A:
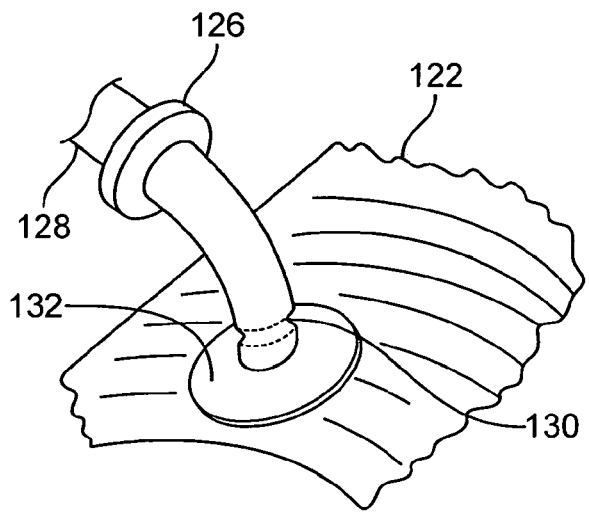
Figure 18B:
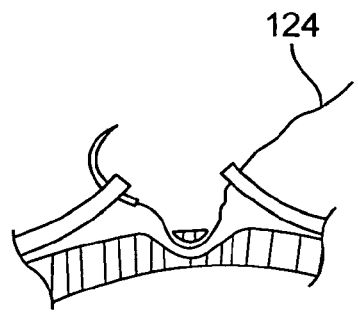
Figure 19:
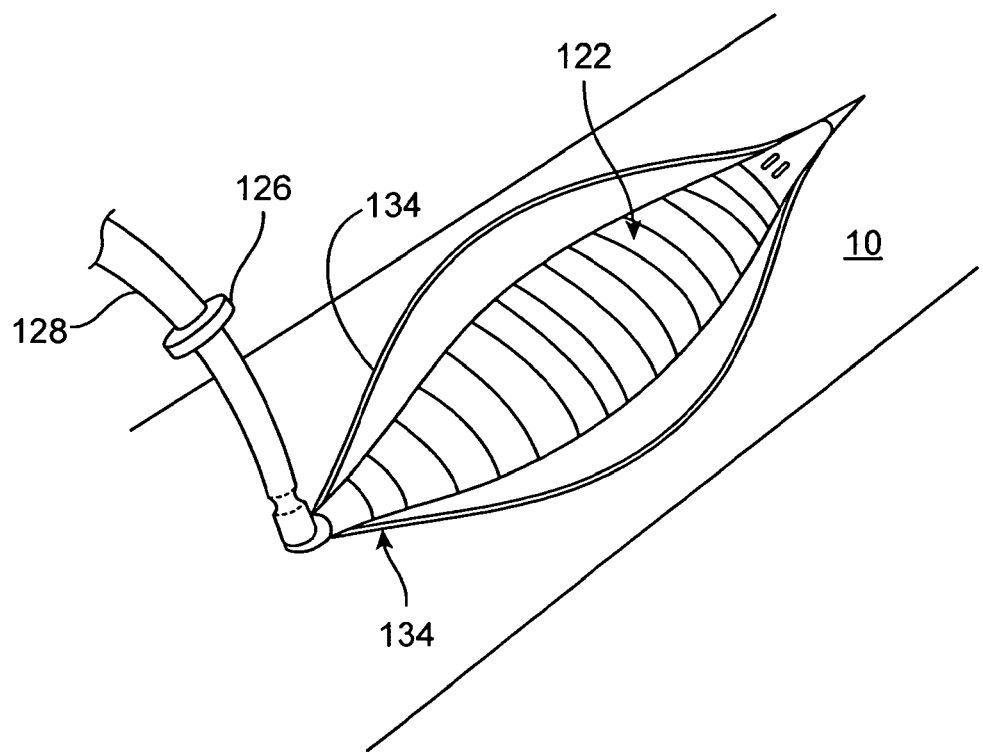
Figure 19A:
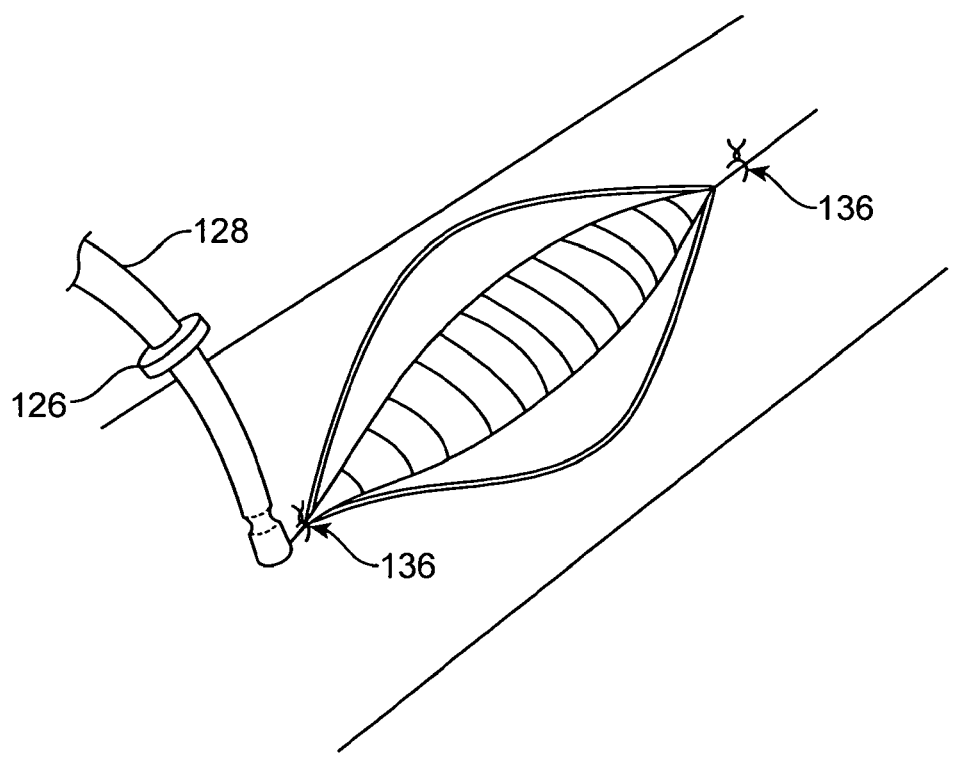
Figure 20:
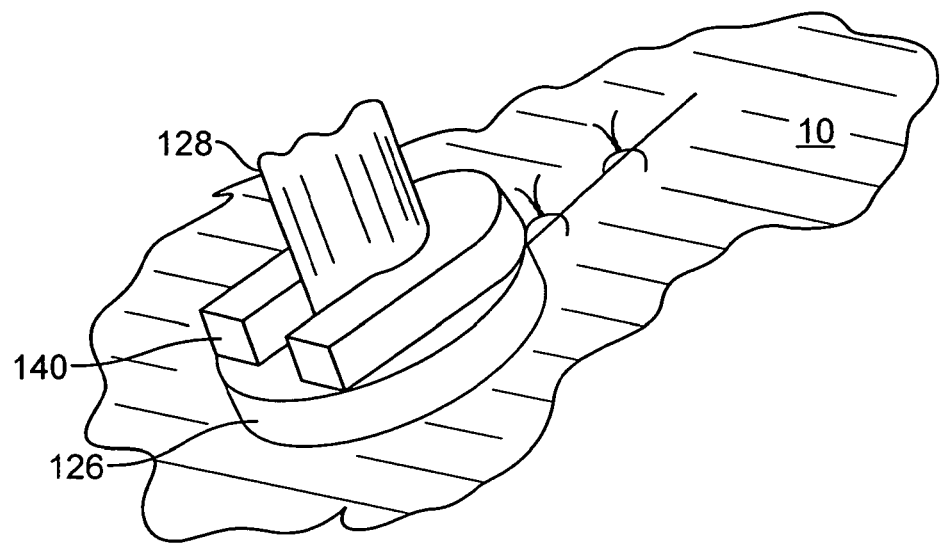
Figure 20A:
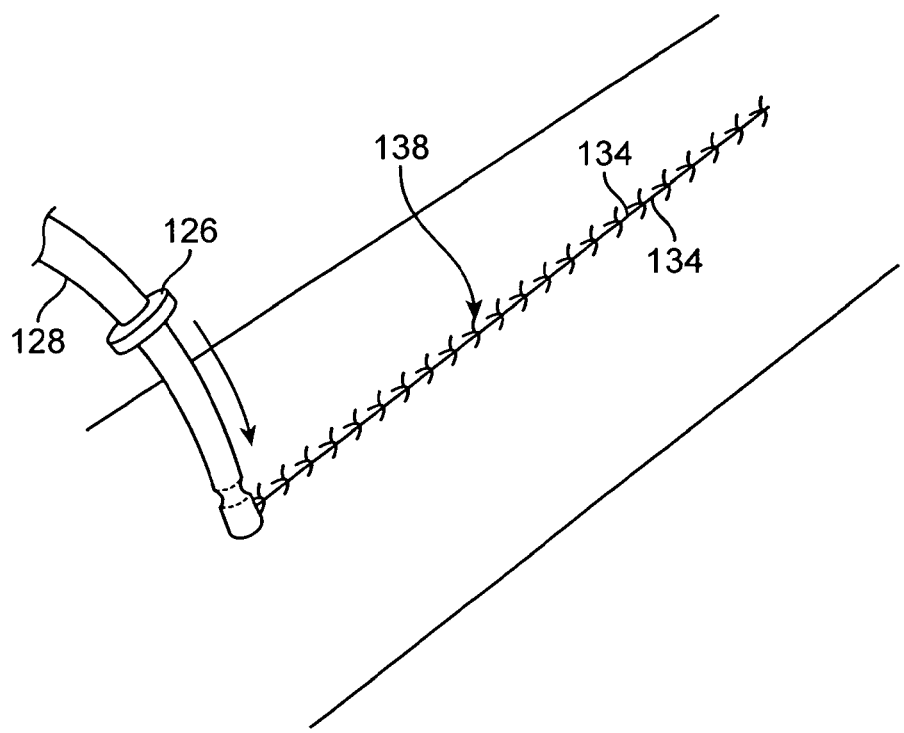
Figure 21:
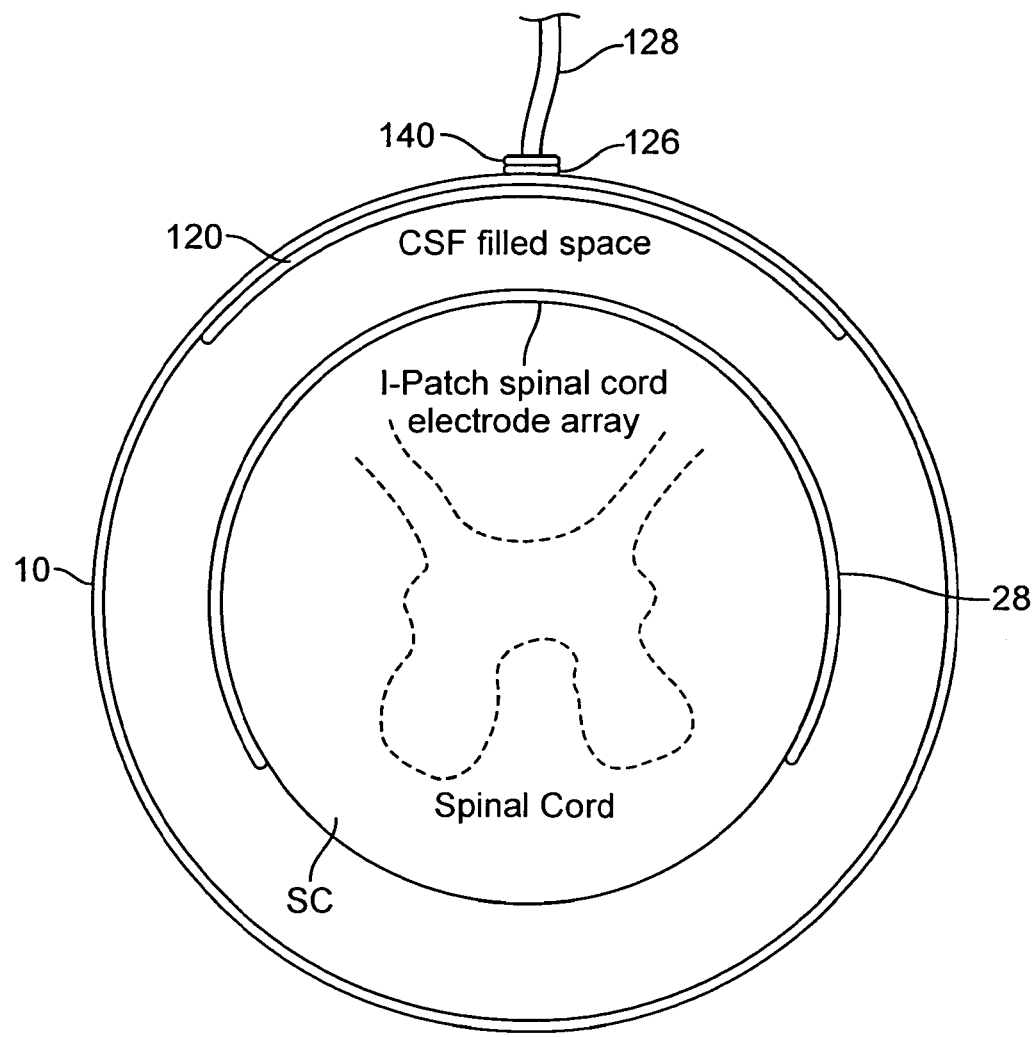

An I-Patch applier (IPA) 90 is illustrated in FIGS. 16 and 17. The IPA 90 will preferably enable the surgeon to maintain a rigid, but reversible attachment to the I-Patch main assembly of receiver 28. While maintaining a rigid attachment of the I-Patch with a main assembly of the IPA 90, the surgeon will have the ability to adjust the position of the I-Patch's pliable attachment arms in an incremental, precisely controlled, and reversible manner. After the I-Patch is placed on the surface of the spinal cord, and the flexible attachment arms are in their final position, the IPA allows the surgeon to safely and efficiently detach the I-Patch from the IPA.

The IPA 90 can be used as a hand-held device, or attached to an intra-operative mechanical advancer device. The surgeon controls the position of the IPA by controlling the insertion device rod 92 (FIG. 16). A stabilizing plate 94 is attached to the end of this rod 92. The plate 94 is contoured to match the curvature of the I-Patch device 28, which in turn is contoured to match the curvature of the spinal cord SC. The I-Patch main assembly contains the transceiver antenna and control circuitry and fits snuggly into IPA stabilizing plate 94.

The I-Patch flexible attachment arms 36 extend away from the main assembly and are contoured to follow the curvature of the spinal cord surface S. The distal ends of these flexible arms 36 can be reversibly extended during the insertion procedure in order for the I-Patch to be placed on the spinal cord SC. This function is achieved by securing a suture through an eyelet 96 positioned at the termination points of the flexible arms 36. A double strand suture 98 is then passed through a series of islets 100 until secured to a suture tension adjustment rod having a knob 102. The surgeon rotates this rod to adjust the conformation of the extension arms. When the I-Patch is being inserted onto the spinal cord, the adjustment rod is rotated into a position that achieves the desired degree of flexible arm extension. Once the I-Patch is in the desired position, the surgeon rotates the adjustment rod until the flexible arms have returned to their pre-formed position, resulting in uniform, gentle, direct contact of the entire I-Patch device with the spinal cord surface. The surgeon then disengages the IPA from the I-Patch by cutting the tension sutures. The cut sutures are gently removed, followed by removal of the IPA. The entire insertion procedure should be accomplished in approximately 15 seconds (FIG. 17).

The I-Patch system will typically include a thin-film extra-dural device 40 that wirelessly transmits power and command signals to the spinal cord electrode assembly 28. This extra-dural device element 40 achieves the following design goals. Optionally, no physical connection between the power/command relay device and the spinal cord electrode (i.e. no 'tethering'). No physical obstruction of the CSF surrounding the spinal cord (avoid risk of syrinx formation). Optionally, no device elements penetrate the dura in a manner that would result in an increased risk of CSF fistula formation. The distance, or gap, across which wireless transmission occurs can be made be as short as possible without compromising the other device design specifications.

The extra-dural relay device 40, however, will be exposed to blood products/plasma serum that always accumulates in the extra-dural space following surgery. In some instances, these materials could accumulate in the space between the extra-dural device and dura, altering the spatial and electromagnetic relationships between the relay device and the spinal cord implant. While this will not usually be a concern, under certain circumstances the electromagnetic coupling between the extra-dural and spinal cord elements may be affected, as it is highly sensitive to relative spatial relationships and the dielectric properties of intervening materials.

An intra-dural relay device (IDRD) 120 as may be used an alternative to the extra-dural relay element 40 and may have superior performance characteristics under certain circumstances. The IDRD 120 includes a thin film power/command relay device body 122 that is placed on the inner surface of the dura lining the dorsal aspect of the spinal canal See FIGS. 18 through 21. The pliable thin film device 122 contours to the curved surface of the dorsal spinal canal dura and is held in place with sutures 124. It is placed after the spinal cord electrode array device 28 is positioned, at the beginning of the dural closure procedure. The dural closure procedure does not differ significantly from the standard closure procedure. The risk of CSF leak around the lead cable emanating from the thin film IDRD is eliminated by using a simple 'washer' clamping method at the lead cable exit site. Following surgery, the IDRD body 122 will lay flush with the inner surface of the dura. The IDRD's low profile will not obstruct CSF flow. The spatial relationship between the IDRD and spinal cord electrode array will not be altered by the post-operative accumulation of blood products in the extra-dural space. The surgical technique for suturing closed the dura will not differ significantly from that used with the 'standard' I-Patch procedure. Only additional seconds are required to place the 'washer' and crimping device, such as by sliding a dual compression washer 126 along a flexible lead 128 beyond a groove 130 so as to secure the washer in position by a clamping or washer compression device 140, with the dura clamped between the washer 126 and a flanged, flat backstop 132 of IDRD body 122. The IDRD 120 can be secured in position under the surface of dura 10 within cut dura edges 134 with stay sutures 136 placed at proximal and distal ends of the IDRD body 122. Dural edges 134 can be approximated by sutures 138, and washer 126 can then be slid along lead 128 beyond groove 130 so that the crimp or washer compression device 140 engages the groove.

Figure 22:
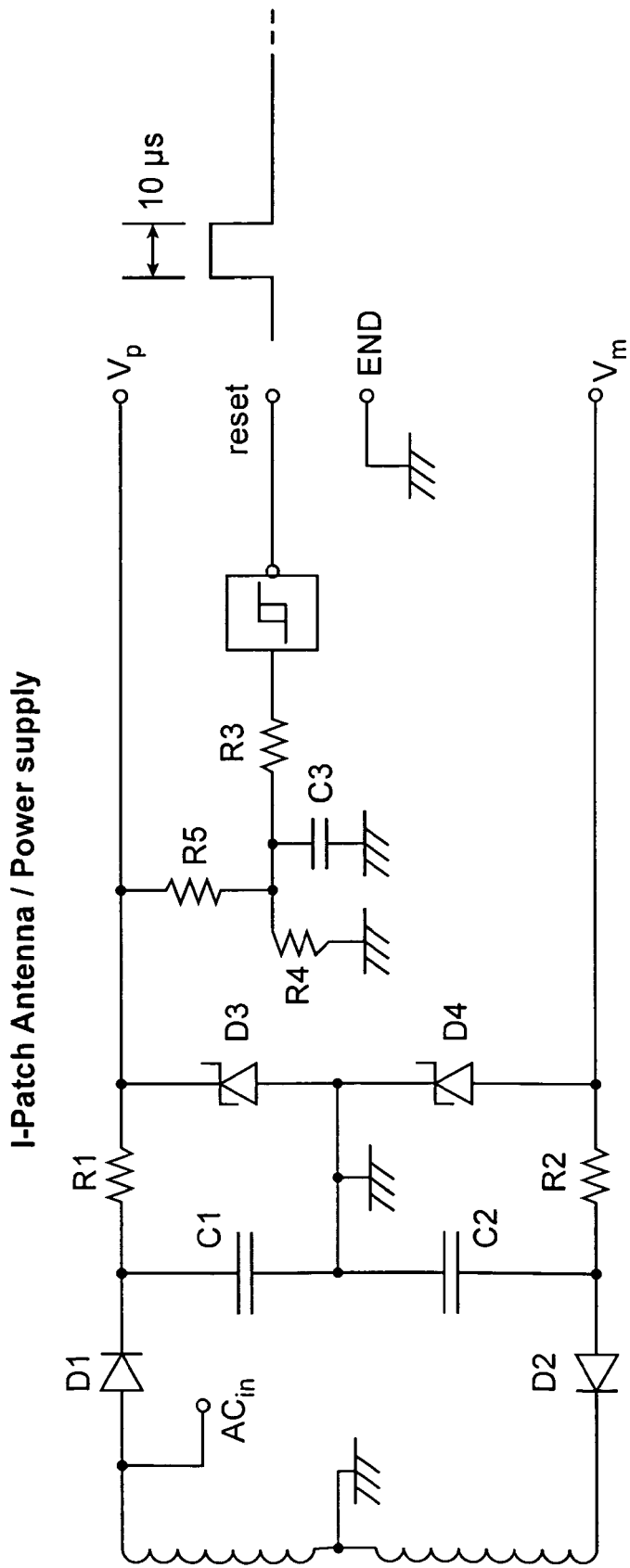
FIGS. 22 and 23 show exemplary schematic diagrams of one embodiment of the circuitry that might be incorporated onto the I-Patch implant
Figure 23:
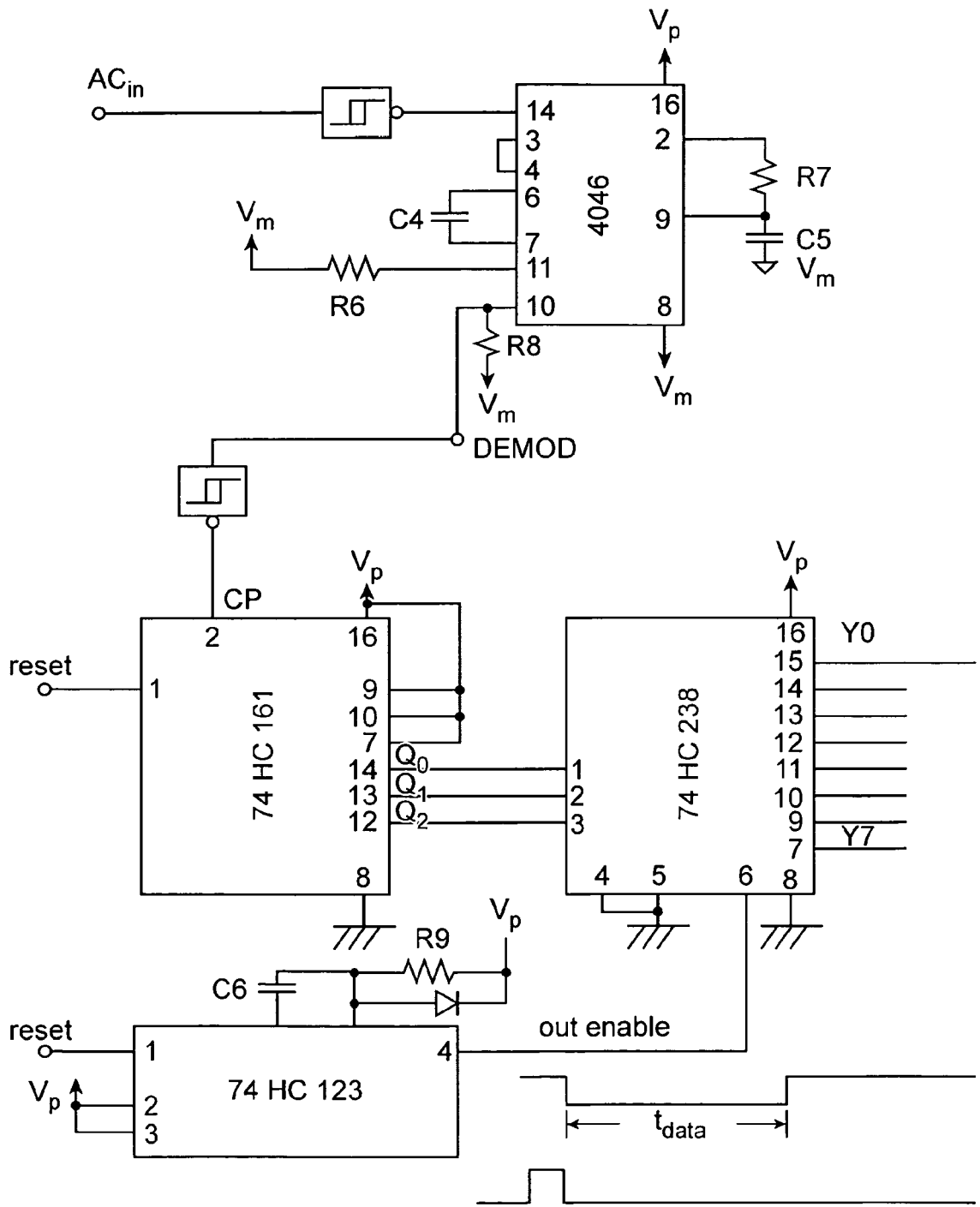

FIGS. 22 and 23 show one embodiment of the electronic elements that might be on-board the I-Patch spinal cord implant. FIG. 22 shows the transceiver coils that inductively couple power and information signals into the circuit. A bridge circuit converts the ac signals to dc voltage levels, in order to provide power to the rest of the circuit. A reset signal is generated from the input pulses via a Schmitt trigger. FIG. 23 shows the other elements of the control and pulsing circuit. These consist of a phase-locked-loop that generates a pulse train which is operated on by a counter, and a 3-bit to 8-line decoder that, with a monostable multivibrator, converts the counter's wavetrain into signals that are distributed to selected electrodes. The above-mentioned reset signals are used to clear the circuit elements at the end of each pulsing cycle.

Figure 24:
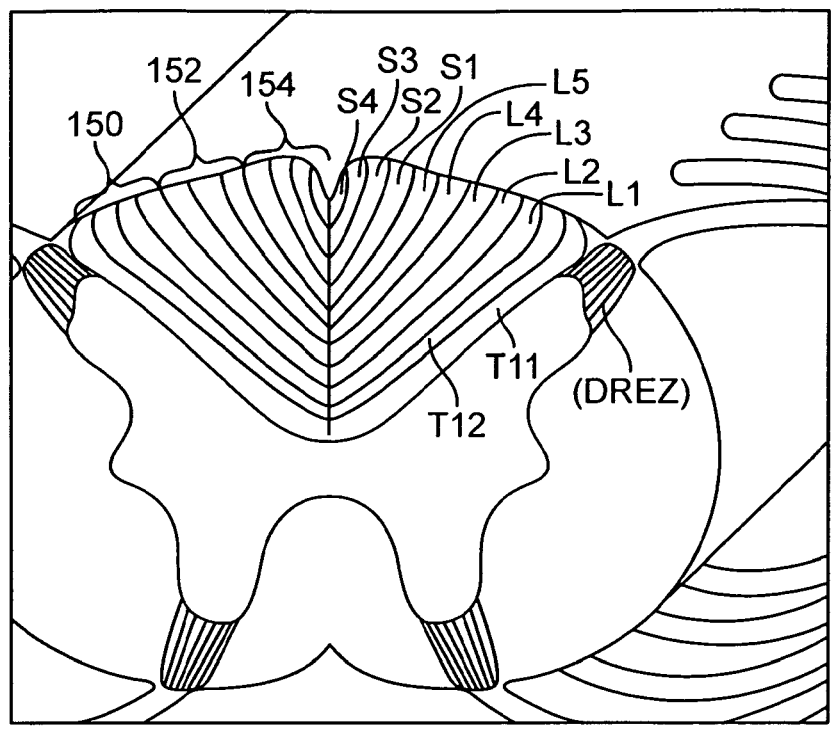
FIG. 24 shows the postulated somatotopic organization of the dorsal spinal column axons.

FIG. 24 shows the somatotopical organization of the dorsal spinal column axons. Embodiments of the devices, systems, and methods described herein may make use of such organization by selectively energizing electrodes of the array structure 28 so as to inhibit focal pain of (or otherwise treat) somototopically corresponding anatomy of the patient. Axial regions T11, T12, L1, and L2 are associated with low back signals 150; L3, L4, and L5 are associated with leg and foot signals 152; and S1-S4 are associated with pelvis signals 154; so that stimuli applied to one of these regions may provide therapeutic effects for pain of the associated anatomy. Note that limiting lateral transmission of stimuli by employing direct contact or near field signal transmission from a discrete electrode of the array to the spinal cord may be particularly beneficial for treatment of low back pain or the like, as the axons associated with low back pain may be located in close proximity to the dorsal root entry zone DREZ, and inhibiting transmission of spurious or collateral signals to the DREZ may improve the efficacy and/or decrease deleterious effects of the therapy.

Figure 25:
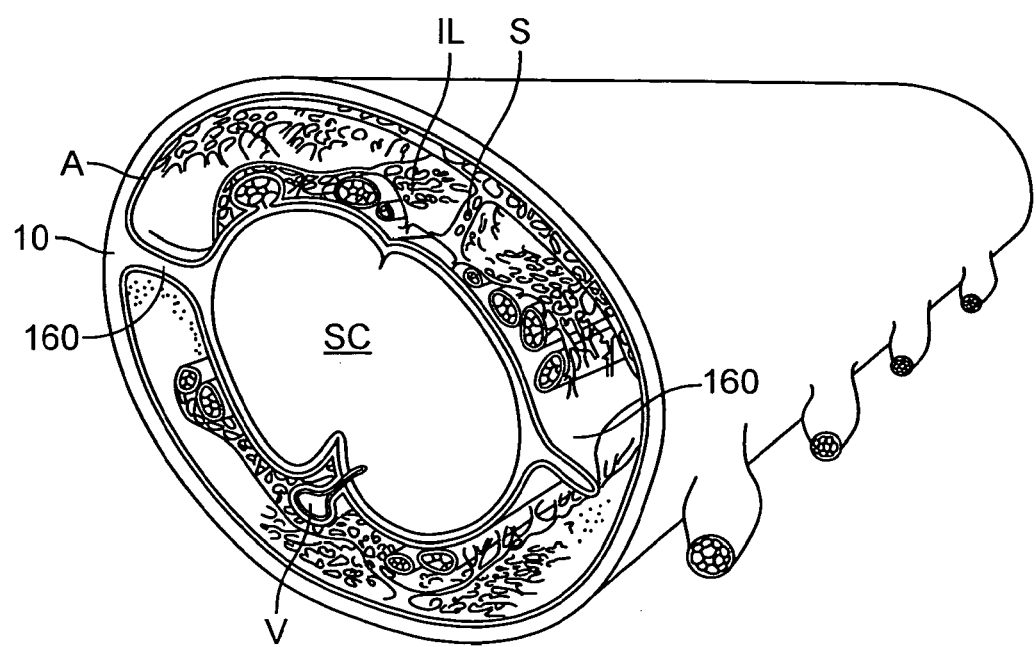
FIGS. 25 and 25A show a perspective view and an axial view of the anatomical arrangement of the spinal cord tissues, including the presence of the dentate ligaments which support of the spinal cord within the spinal canal.
Figure 25A:
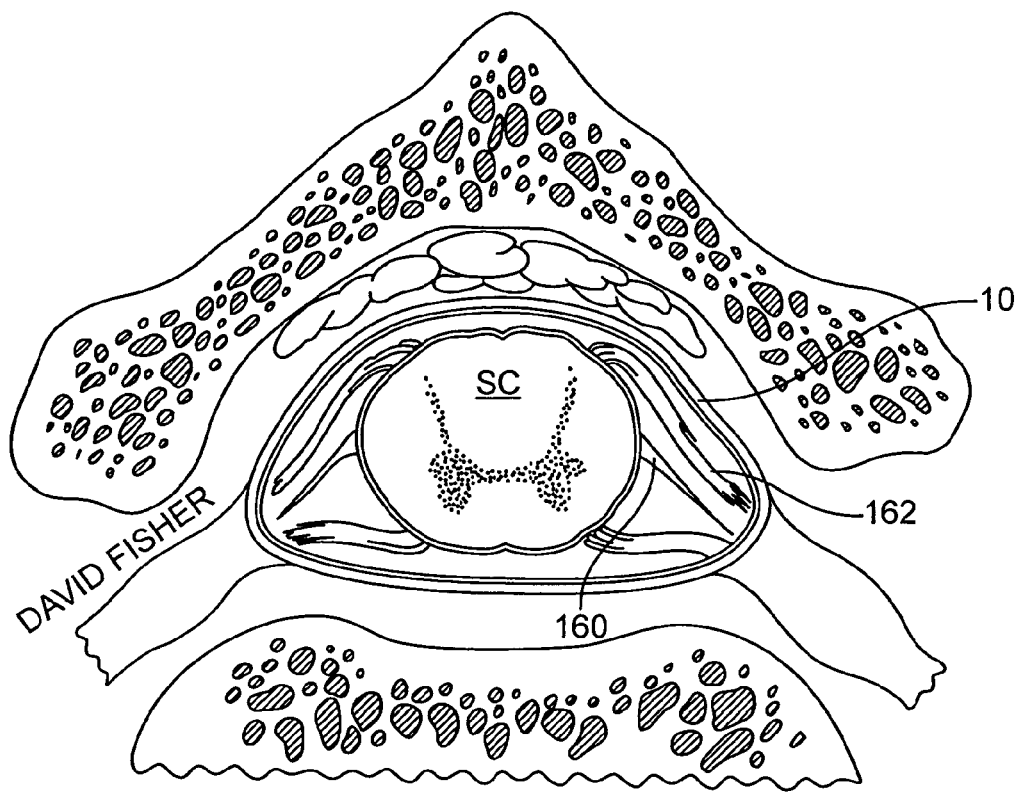

FIGS. 25 and 25A show dentate ligament structures that extend laterally between the spinal cord and surrounding dura. More specifically, FIG. 25 is a profile-view diagrammatic representation of the human spinal cord with surrounding meninges. Arachnoid mater A is closely applied to the thick outer dura 10. An intermediate leptomeningeal layer IL lies between the arachnoid mater A and the pia mater. This layer is fenestrated and is attached to the inner aspect of the arachnoid mater. It is reflected to form the dorsal septum S. Dentate ligaments 160 are present on either side of the spinal cord SC. The collagenous core of the dentate ligaments fuses with subpial collagen medially and at intervals laterally with dural collagen, as shown on the left side of the diagram. Blood vessels V within the subarachnoid space are seen along a surface of the spinal cord SC. As can be seen in the axial section through the spinal cord of FIG. 25A, dorsal rootlets 162 and ventral rootlets 164 may extend from spinal column SC dorsally and ventrally of denticulate ligaments 160, with the dentate ligaments generally attaching the left and right lateral portion of the spinal cord SC to left and right regions along an internal surface of dura 10. Additional details regarding these anatomical structures may be understood, for example, with reference to "The Fine Anatomy of the Human Spinal Meninges" by David S. Nicholas et al.; J. Neurosurg 69:276-282 (1988); and to "The Denticulate Ligament: Anatomy and Functional Significance" by R. Shane Tubbs et al.; J. Neurosurg 94:271-275 (2001).

Figures 26, 26A:
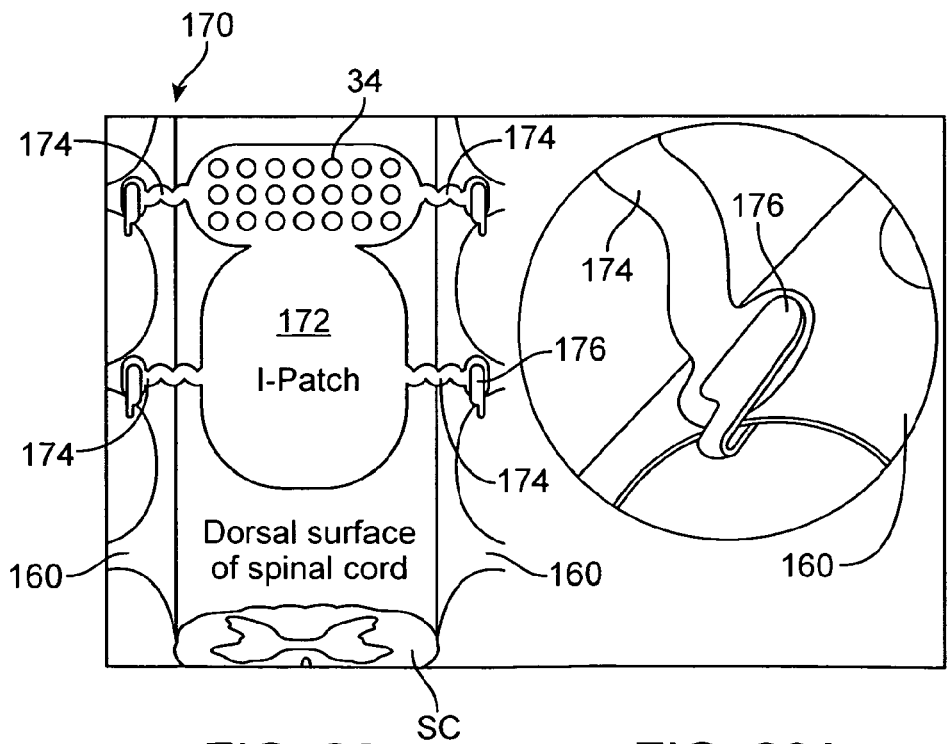
FIGS. 26 and 26A show a top down or dorsal view of an alternative embodiment of an I-Patch supported on a dorsal surface of a spinal cord by fixation to a dentate ligament so as to support the I-Patch, respectively.

FIGS. 26 and 26A show yet another alternative embodiment of an I-Patch 170 having an electrode array 34 supported by a body 172 including a flexible substrate or backing as described above, with the array here configured to engage a dorsal portion of the spinal cord SC. Dentate ligament attachment features such as flexible arms 174 extend laterally from left and right sides of body 172, with the arms optionally comprising the same substrate or backing material from which the body is formed. These arms or other features are configured to be attached to left and right dentate ligaments 160 on either side of the treatment region of the spinal cord so as to support the array 34 in engagement with the surface of the spinal cord.

The dentate ligament provides a thin, but high tensile strength fibrous attachment that extends from the lateral spinal canal wall to fuse with and attach to the pia-arachnoid membrane on the lateral surface of the spinal cord, approximately at the 'equator' of the cord as viewed in cross-section. This location and geometry is well suited for gently exerting a desirable amount of downward/inward pressure on the I-Patch, optionally without having to resort to sutures and without using any 'non-targeted' parts of the spinal cord as points of attachment. The body of dentate-ligament supported I-Patch device 170 may be largely or entirely flexible and/or elastic. Electrodes 34 may be arrayed to provide coverage within the dorsal column of the spinal cord and may be embedded in a flexible silicone-type, biocompatible material. The dentate ligament attachment features such as attachment arms 174 may be more highly elastic, optionally having no electronic elements contained within them, and may extend laterally from the electrode-bearing body portion of the device. These attachment arms can be thin (optionally being thinner than the substrate adjacent the electrode array), flat, and/or floppy. The attachment arms may 'flair' to a larger width adjacent the ends opposite the array, and/or may have slightly raised groves or texture at or near these ends to facilitate clipping, crimping, and/or adhesively bonding the arms to the dentate ligament.

During implantation, the dentate ligament supported I-Patch device 170 may be placed and centered over the exposed dorsal column of the spinal cord. A small number of rootlets may optionally be sectioned to create room for the attachment arms (as may also be done with other I-Patch embodiments). The flared end of each attachment arm can be draped on the dentate ligaments on either side of the spinal cord. With the patient in the prone position the gravitational forces will result in a gentle fit of the electrode bearing portion of the I-Patch on the dorsal spinal cord. The amount of downward gravitational force exerted on the I-Patch will not be large enough to occlude surface blood vessels. The preferred points of contact will be between an array of slightly protruding electrode contacts and the pial surface of the dorsal columns. Microclips 176 or other types of fixation or crimping devices can be used to secure the attachment arms to the dentate ligaments. Metal microclips used in a variety of surgeries (e.g. Weck Clips) may be employed, though non-metallic clips or other fasteners may have particular advantages, and are used widely for endoscopic surgical procedures. A relatively broad surface of attachment is beneficial because of the thin, almost spider web nature of the dentate ligament. An approximately 3 mm clip may, for example, be employed. Alternatively, a tissue glue could be used. With many techniques, there is no requirement for the I-Patch, or I-Patch attachment arms to be jostled or manipulated into position. The device is simply draped on the dorsal spinal cord surface and dentate ligaments, and secured in place. With these embodiments, the 'point of attachment' or 'anchor point' of the device may be on connective tissue rather than spinal cord tissue, limiting the clinical significance of any damage to the supporting tissue structure.

Figure 27:
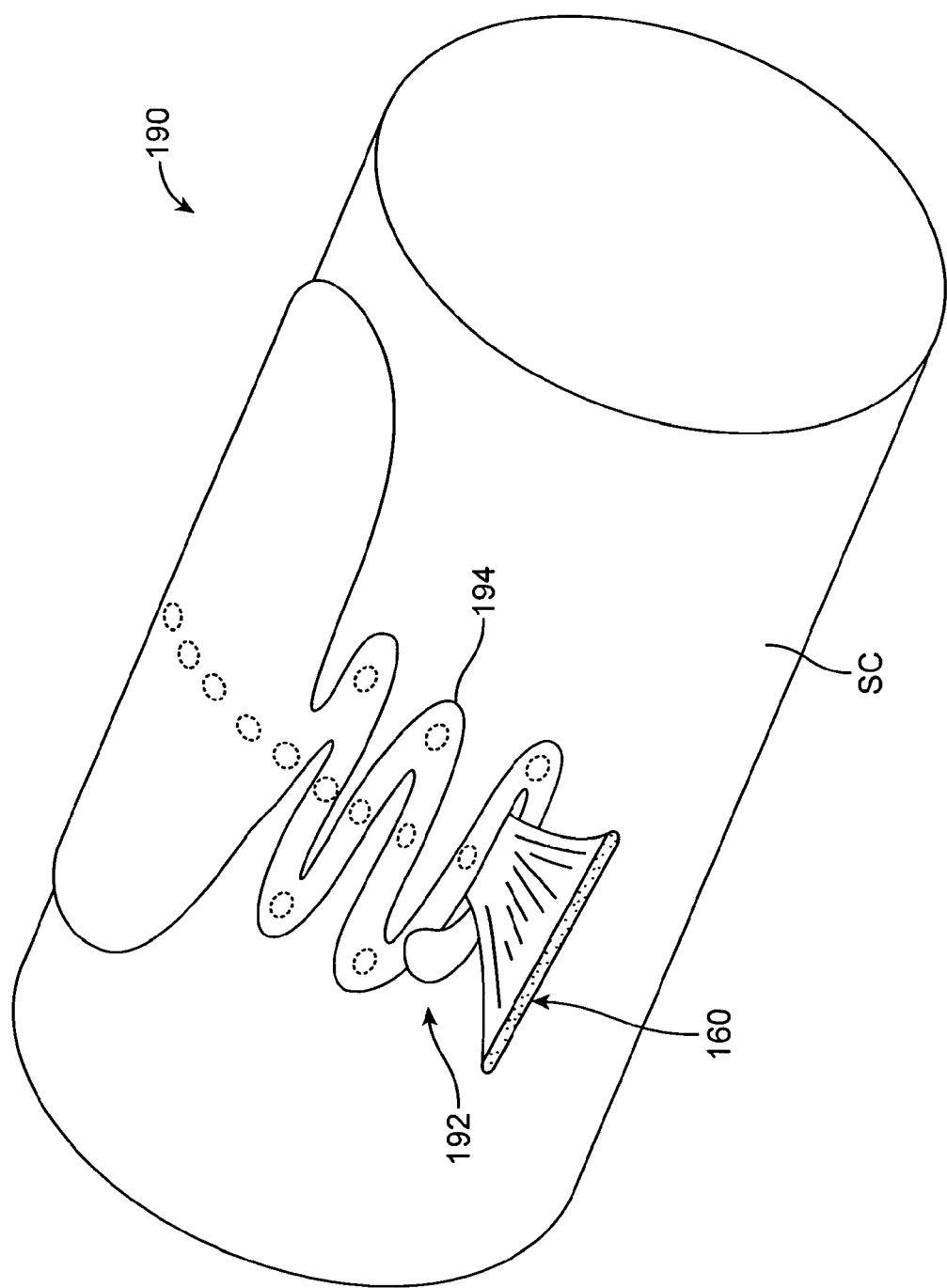
FIGS. 27 and 27A show a perspective view and a plan view of yet another alternative embodiment of an I-Patch configured to be supported by arms that clamp to dentate ligaments on either side of the spinal cord.
Figure 27A:
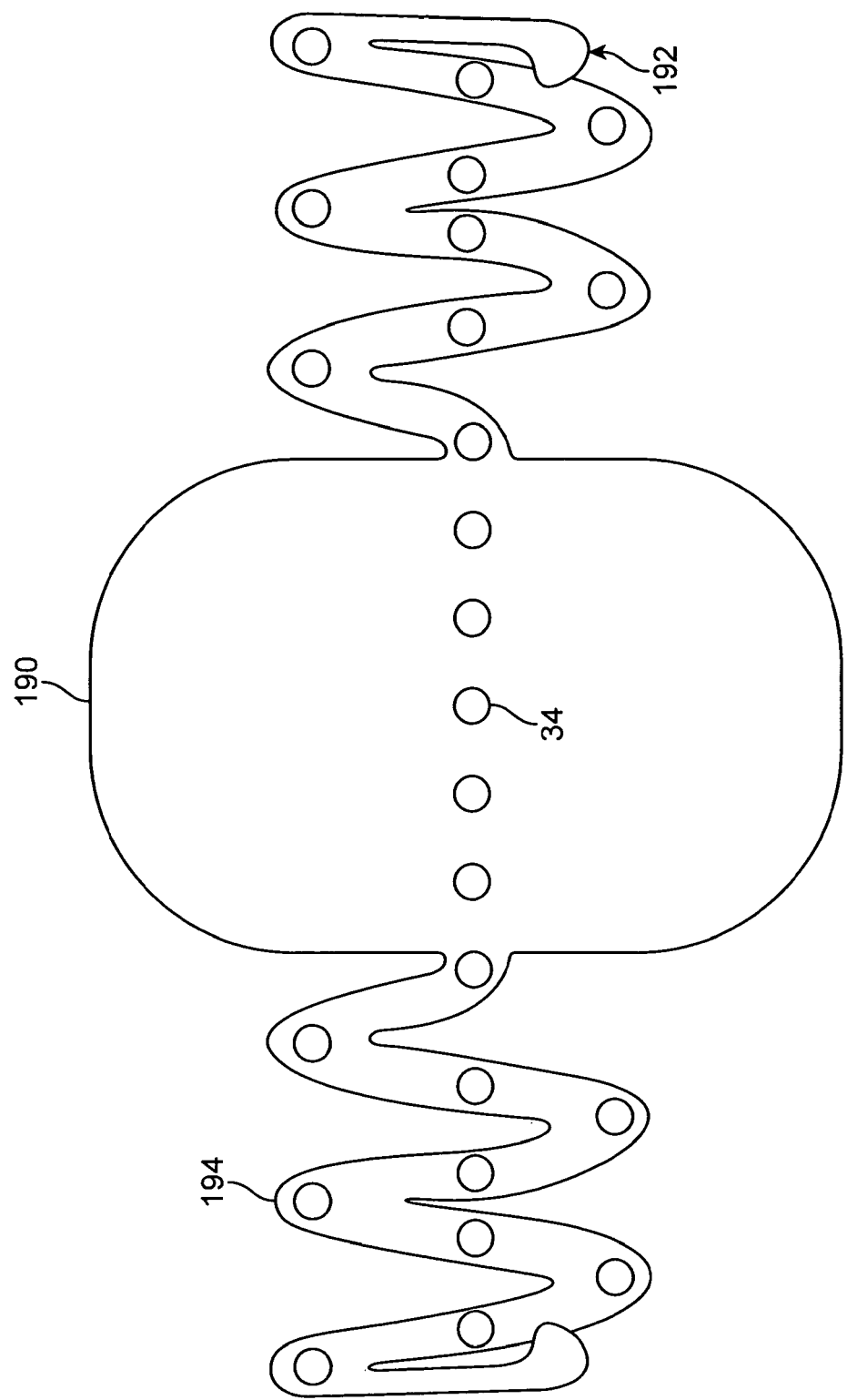

A variety of alternative dentate ligament-supported I-Patch embodiments may be provided, including embodiment 190 of FIGS. 27 and 27A. In general, these embodiments of the I-Patch should be highly flexible so as to avoid restricting normal spinal cord pulsations in-situ. Firm, constant mechanical contact should be achieved between the electrode surfaces and the pial surface of the spinal cord. A 'one size fits' all design is desirable, whereby a standard device can accommodate almost the full range of spinal cord anatomy variants encountered in patients, and/or where a limited number of sizes (1-5) will span a significant patient population. The implantation procedure should be simple, safe, fast and un-complicated. Toward that end, embodiment 190 makes use of the dentate ligaments 160 to serve as a purchase point for a malleable I-Patch electrode array. There is a simple clasp 192 at the end of each malleable or plastically deformable I-Patch attachment arm 194. In the operating room, the surgeon secures the ends of each attachment arm 194 to the dentate ligaments 160. These ligaments are comprised of connective tissue and have no innervation. They are firmly attached to the lateral margin of the spinal cord. The highly elastic/malleable I-Patch electrode assembly 190 is thus secured to the spinal cord surface. Advantages of this and/or other dentate ligament supported I-Patch variants may include a relatively simple electrode design. Also, these embodiments should result in excellent mechanical contact between electrodes and pial surface, as the dentate ligaments will easily withstand the chronic forces exerted on them by the I-Patch. The variability provided through deformable arms may allow a 'one size fits all' (or limited number of sizes) in the device, and the implantation procedure may be relatively less complicated. Penetrating electrodes may optionally be employed in place of the contact electrodes, with the body of many of the dentate ligament embodiments optionally providing a pial surface platform to which such electrodes could be mounted.

Figure 28:
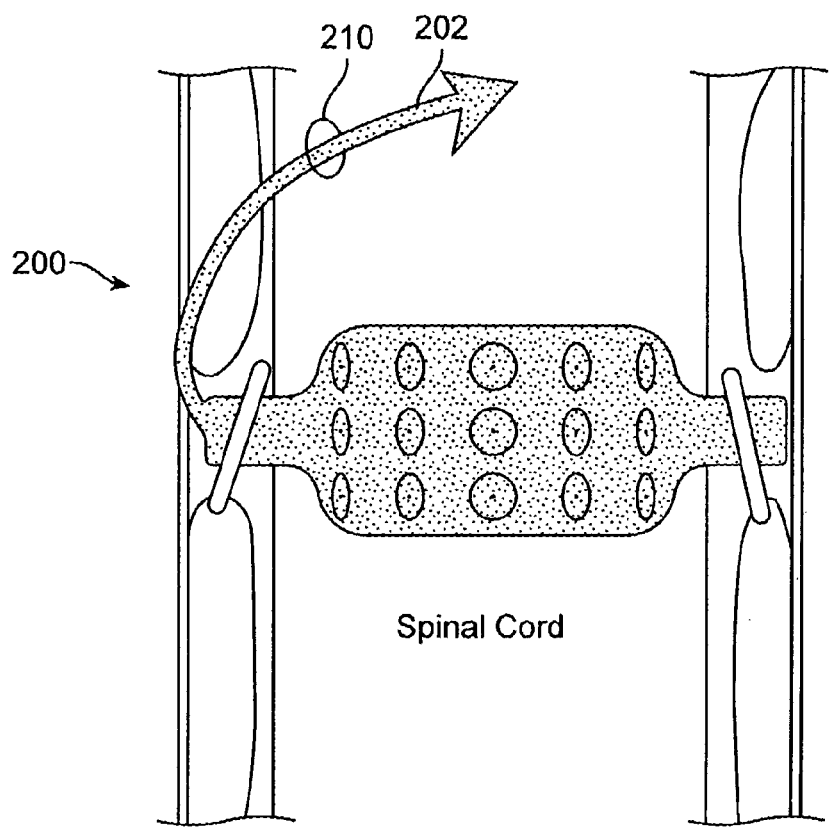
FIGS. 28 to 28F illustrate a still further 'wired' alternative embodiment of an I-Patch secured to dentate ligaments, along with implantation of the device so that a lead extends along (and is attached to) one of the dentate ligaments and is sealed where it extends through the dura.
Figure 28A:
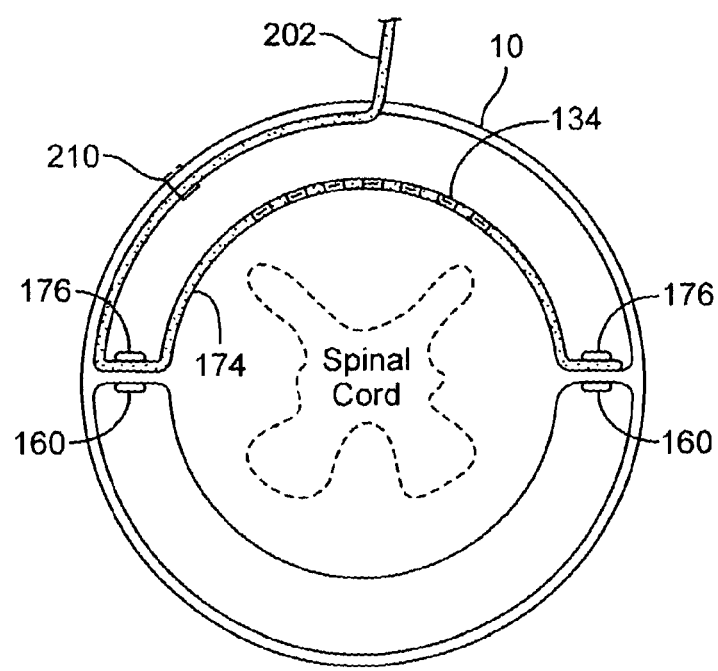
Figure 28B:
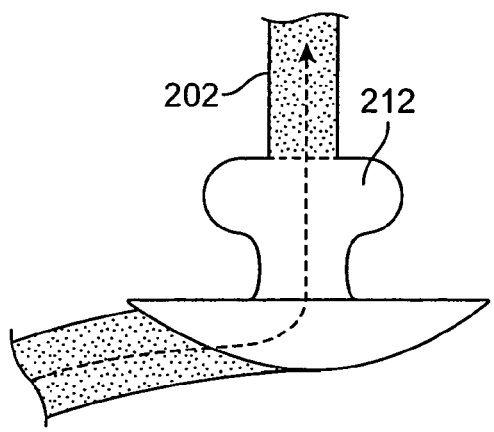
Figure 28C:
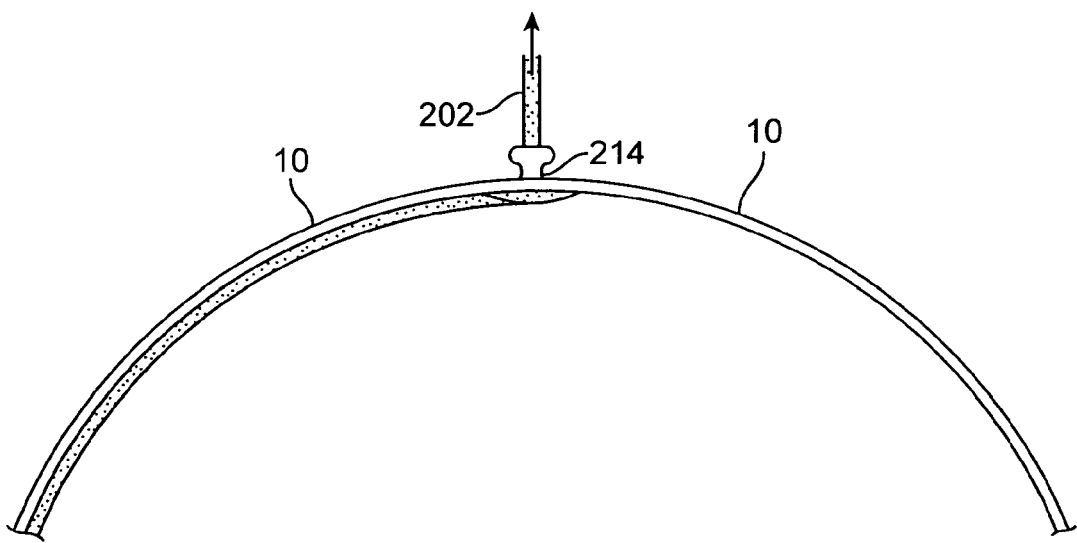
Figure 28D:
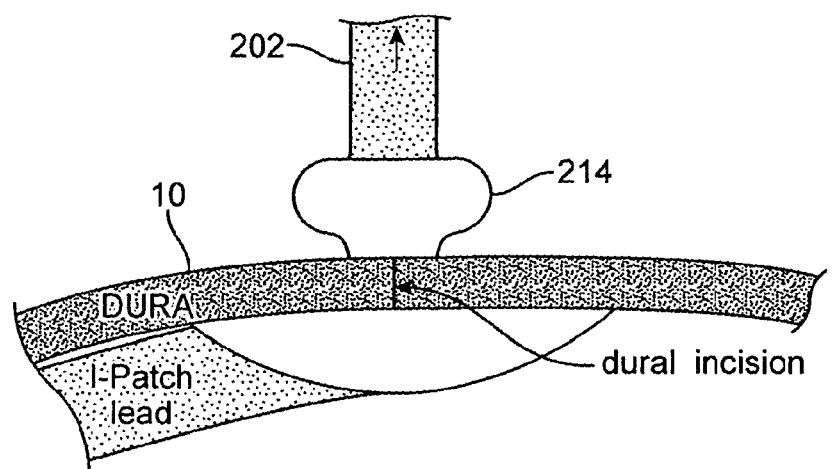
Figure 28E:
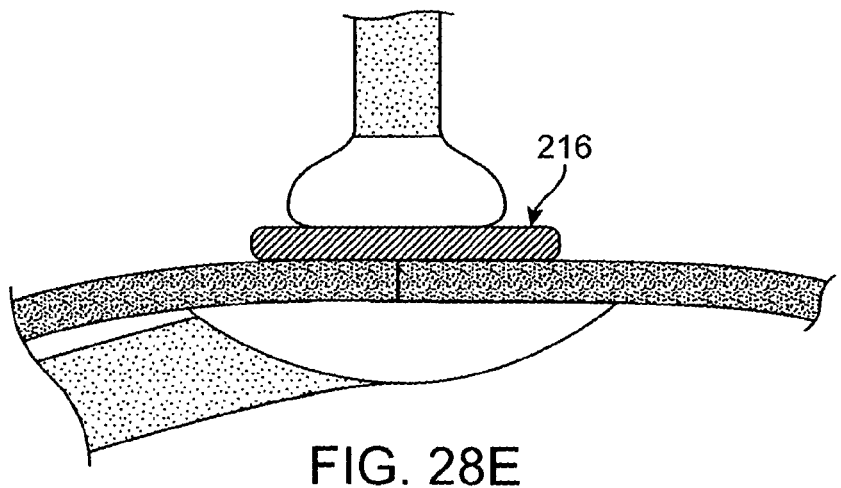
Figure 28F:
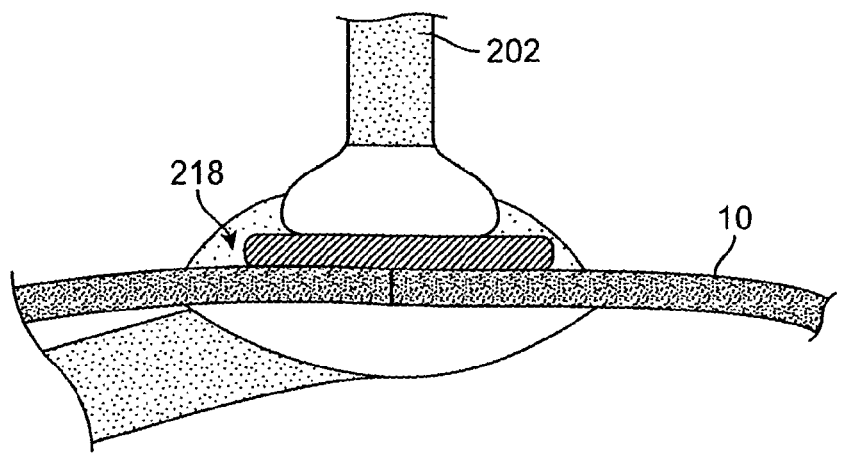

FIGS. 28 to 28F illustrate a still further 'wired' alternative dentate ligament (DL) supported embodiment of an I-Patch 200, along with implantation of that device so that a lead extends along (and is attached to) one of the dentate ligaments and is sealed where it extends through the dura. Wired DL I-Patch 200 has a flexible lead that extends through dura 10, with the lead preferably extending along one of the DL attachment arm 174. The lead then optionally runs laterally and dorsally, hugging the inner surface of the dura 10, optionally using a staple, clip, suture, or stapled bracket 210 to maintain the position of the lead against the dura. The lead 202 may exit the dura 10 along the midline. By placing crimping clips 176 to secure the lead bearing I-Patch attachment arm 174 to the DL 160, a strain relieving function will be achieved. This should prevent torquing on the I-Patch by the leads and injury to the spinal cord with spinal cord movement. As shown in FIGS. 28B to 28F, a dura-traversing lead fitting 212 can help inhibit lead migration and facilitate water-tight dural closure, with the lead optionally being disposed along a re-approximated mid-line durotomy.

Figure 29:
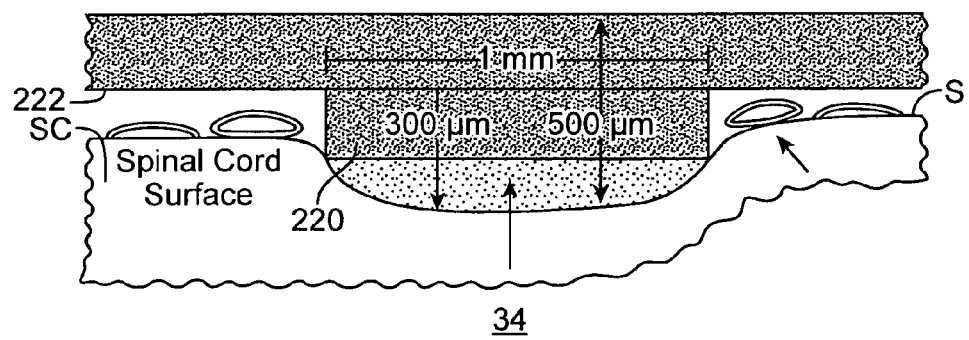
FIG. 29 schematically illustrates an electrode extending from an interior surface of a backing or substrate of an array structure of the I-Patch.

FIG. 29 schematically illustrates an electrode extending from an interior surface of a backing or substrate of an array structure of the I-Patch. The therapeutic benefit of the I-Patch to the patient may be enhanced by maximizing the SCS current densities in the targeted conducting tracts of the spinal cord itself, while minimizing the current density shunted away by the CSF. This benefit may be enhanced by engaging the electrodes against the surface of the spinal cord as shown, with a stand-off column 220 extending between the exposed portion of the electrode 34 and the underside of the implant substrate body 222. This can support the implant off the surface S of the spinal cord SC by about 100 µm to accommodate micropulsations of the spinal cord, as described above. By insulating the surface of stand-off column 220, it is possible to minimize the shunting effect of the CSF, as the exposed portion of the electrode will be in contact only with the pial surface of the spinal cord, and not with the CSF itself. Gentle inward pressure causes slight inward "dimpling" of the pial surface by the electrode. As a result, the un-insulated (active) exposed surface of the electrode is "sealed" by spinal cord tissue enveloping the protruding portion of the contact. A small gap separates the electrically inactive portions of the I-Patch device, providing space into which the spinal cord tissue may expand and contract with cardiac pulsation cycles.

Figure 30:
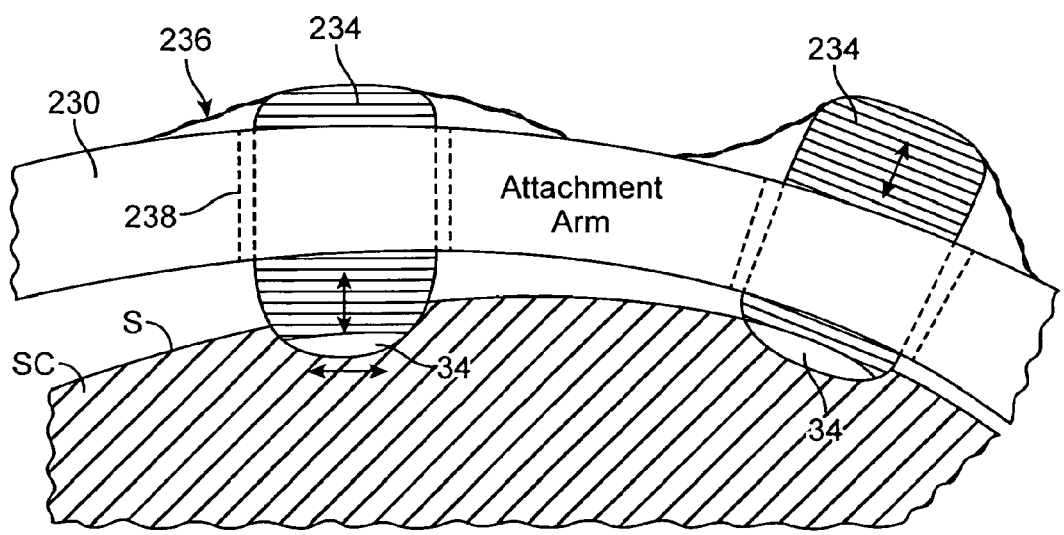
FIG. 30 schematically illustrates individual electrodes flexibly mounted to a backing or substrate by a soft resilient material so as to allow the electrode to float and inhibit sliding movement of the electrode against a surface of the spinal cord during pulsation.

FIG. 30 schematically illustrates individual electrodes 34 flexibly mounted to a backing or substrate 230 by a soft resilient material 232 so as to allow the electrode to resiliently float or move radially and/or laterally relative to the substrate by a distance that is at least as large as the pulsations of the surface S of spinal column SC. This movement of the individual electrodes may inhibit sliding engagement of the electrodes against the surface of the spinal cord during pulsation. In some implementations of the I-Patch the only parts of the I-Patch device that directly engage the spinal cord are the electrode contacts. These may serve as mechanical anchoring points for the device. They should exert just enough pressure to maintain good electrical contact with the surface of the spinal cord. The pressure exerted on the spinal cord by the contacts should be generally even for all of the contacts. Some embodiments achieve this by having electrodes protruding slightly from contoured attachments arms. These contoured attachment arms position all contacts in the desired position relative to the surface of the spinal cord. Outward and inward movements of the contacts (e.g. with pulsations and respirations) are accommodated by movements of the semi-rigid attachment arms. Unfortunately, this makes significant demands on the mechanical characteristics of the attachment arms. The arms may benefit from being contoured to a spinal cord of individual patients, and they should be constructed of materials that both hold this contour for a decade or more, yet expand and contract to accommodate spinal cord expansion/contraction.

The mobile electrode approach facilitates design and material performance goals of the attachment arms. Each contact is mobile and attached to the I-Patch via an elastic/spring-like interface. The degree to which each contact extends out from the attachment arm is determined by the distance separating the attachment arm from the spinal cord surface at each contact location. The elastic nature of the connection between each contact and the attachment arm/body cause each contact to independently protrude out from the device until the desired tissue contact/force interface is achieved. In this way desirable mechanical interfaces are achieved between some, most, or all electrode contacts and the spinal cord, even if the attachment arms/body do not conform perfectly to the shape of the spinal cord. Also, the elastic interface allows the contacts to slide in and out with expansion/contraction of the spinal cord without attachment arm movement. With mobile contacts, the attachment arms can be more rigid and will not be required to perfectly follow the contour of each patient's spinal cord.

In the embodiment of FIG. 30, electrode bodies 234 extend through apertures 238 in substrate 230, with the substrate being pliable and having elasticity appropriate to supporting thin film circuit components. A soft elastomeric material 236 spans the apertures from substrate 230 to the electrode bodies, with the elastomeric material here comprising a sheet of material adhered to the outer surface of the substrate. In other embodiments, the electrodes may be supported relative to each other and the substrate with a soft elastomeric material spanning directly between the electrode and walls of the aperture (such as by insert molding the material into the apertures with the electrode bodies positioned therein). In still further alternative embodiments, the resilient material may form column 220 or the like. Flexible conductors (not shown) may extend between the substrate and electrode bodies within or outside the elastic material with these conductors optionally being serpentine, having loops, or the like to accommodate movement of each electrode body relative to the substrate.

As can generally be understood from the description and the parent provisional application, embodiments of the invention provide an implantable electronic system including and/or consisting of a signal generator means and a signal transceiver means. The transceiver means conforms to a surface structure of a region of spinal cord in a patient. The transceiver means is able to receive signals wirelessly from said signal generator means, and to process said signals according to an algorithm. The algorithm is then able to cause said transceiver means to generate electrical stimuli according to said algorithm. Said stimuli can be applied by electrodes of said transceiver means to selected points on the surface of said spinal cord in said patient.

Optionally, the transceiver means may include and/or consists of an electronic circuit, a pliable substrate containing said electronic circuit, a plurality of contact points that apply said stimuli from said circuit to said spinal cord, and attachment arms that hold said pliable substrate in non-damaging contact with said spinal cord.

In some embodiments, said generator of said wireless signals consists of a signal production means and an inductive coupling means such as a planar coil prepared on the surface of a pliable substrate. In some embodiments, said planar coil of said signal generator means is configured and positioned so as to conform to the inner or outer surface of a region of the dura mater surrounding the spinal cord. In some embodiments, said planar coil of said signal generator means deployed on a region of said dura mater of said spinal cord and said transceiver means deployed on the actual surface of said region of said spinal cord are positioned in proximity to each other and separated only by the thickness of said dura mater itself and/or by the layer of cerebrospinal fluid filling the gap between said inside surface of said dura mater and said outer surface of said transceiver means which is in intimate contact with said region of spinal cord.

In some embodiments, said planar coil of said signal generator means communicates inductively with an opposing coil that is part of said electronic circuit means on said transceiver means in order to transfer electrical power and electrical control signals from said generator means to said transceiver means, as in an electromagnetic transformer. In some embodiments, said electronic circuit on said transceiver means further consists of circuit elements that may include an information processing means, a memory means, a bus means, a signal distribution means and other means for executing the function of the device according to the method of the invention. In some embodiments, said information processing means of said transceiver means is able to execute one of a plurality of algorithms that are resident either within said memory means of said transceiver or within said generator, with said algorithm being chosen in response to the physiological and anatomical needs of said patient.

The electrical stimuli produced by said transceiver means in response to the action of said algorithm means can be applied to selected points on said region of spinal cord of said patient in response to the physiological and anatomical needs of said patient. The electrical stimuli produced by said transceiver means are generated as desired for the treatment of intractable pain as might be caused by musculo-skeletal disorders, neoplasms, arthritic degenerations, neurodegenerative disorders, trauma and/or the like.

The circuit of said transceiver may include an assembly of discrete or integrated analog and digital components. The analog circuit elements within said transceiver may include active and passive components. The digital circuit elements within said transceiver may operate on electronic pulses, analog or digitized waveforms, dc voltage levels, and/or combinations thereof. The electronic circuit for said transceiver may incorporate a signal multiplexer that is able to distribute a plurality of stimulus signals to a plurality of electrodes in contact with a spinal cord of a patient. The electronic circuit for said transceiver may incorporate a phase-locked-loop system for detecting, synthesizing or processing a plurality of electronic waveforms, pulses and combinations thereof, for subsequent use in generating and distributing stimulus signals to a plurality of electrodes in contact with a spinal cord of a patient. The electronic circuit for said transceiver may incorporate frequency-shift keying and/or pulse-width modulation means for detecting, synthesizing or processing a plurality of electronic waveforms, pulses and combinations thereof, for subsequent use in generating and distributing stimulus signals to a plurality of electrodes in contact with a spinal cord of a patient. The electronic circuit for said transceiver may contain subcircuits to prevent accidental delivery of excess voltages to the spinal cord of a patient during the normal application of stimulus signals. The electronic circuit for said transceiver may contain ferrite elements to prevent the propagation within the circuit of parasitic or spurious radio-frequency signal components. The electronic circuit for said transceiver means may contain miniature solid-state fuses, fusible links or other such current interrupters, as well as back-up circuits, to protect said transceiver and said spinal cord of said patient from short circuits or other modes of failure. The electronic circuit for said transceiver may contain capacitive or inductive energy storage to allow for uninterrupted synthesis and application of stimulus signals in the event of interruption of the power transfer process.

While exemplary embodiments of the devices, systems, and methods have been described in some detail for clarity of understanding and by way of example, a variety of changes, modifications, and adaptations will be obvious to those of skill in the art. Hence, the scope of the invention is limited solely by the appended claims.

What is claimed is:

1. A system for treating pain in a patient, comprising:
   (1) an electrode assembly configured for intradural implantation, which includes:
      (a) a compliant backing;
      (b) a plurality of electrodes forming an array along a surface of the backing;
      (c) a support structure configured to secure the electrodes directly in contact with the spinal cord; and
   (2) circuitry configured for electrical coupling with the electrodes to deliver electrical through the electrodes to a targeted subregion of the spinal cord;
   wherein the electrode assembly is configured to conform to the pial surface of the spinal cord of the patient, and has a sufficiently thin profile such that when the array of electrodes is placed against the pial surface, the CSF filled space is maintained, thereby separating the dura from the spinal cord, preventing mechanical constriction and obstruction of CSF flow between the electrode assembly and the dura; and
   wherein the electrodes are arrayed on the backing so as to provide a sufficiently concentrated stimulus field such that electrical stimuli can be administered to the whole treatment zone from inside the dura without exciting dorsal nerve rootlets.

2. The system of claim 1, wherein individual electrodes in the array are flexibly mounted to the backing by a soft resilient material, thereby allowing each electrode to float resiliently or move radially and/or laterally relative to the backing by a distance that is at least as large as pulsations of the surface of the spinal cord.

3. The system of claim 1, wherein individual electrodes in the array are flexibly mounted to the backing by a soft resilient material such that the electrodes exert generally even pressure on the spinal cord, thereby serving as mechanical anchoring points for the electrode assembly.

4. The system of claim 1, wherein individual electrodes in the array are attached to the compliant backing by way of a stand-off column.

5. The system of claim 1, wherein the electrode assembly is 0.5 mm thin or less.

6. The system of claim 1, further comprising a signal receiver disposed along the backing of the electrode assembly and configured to receive energy wirelessly, and a signal generator having a signal transmitter configured for transmitting energy to the electrodes from outside the patient's dura.

7. The system of claim 1, further comprising a signal generator configured for transmitting energy to the array of electrodes from outside the patient's dura, and a conductor extendable through the patient's dura to couple the generator to the electrodes.

8. The system of claim 7, further comprising a dura-traversing lead fitting that is configured to form a water-tight closure when the dura is closed around the conductor.

9. The system of claim 1, wherein the backing of the electrode assembly contains electronic circuitry configured to prevent accidental delivery of excess voltages to the spinal cord of a patient during normal application of stimulus signals.

10. The system of claim 1, wherein the electrodes are configured to penetrate into the spinal cord and activate neural motor pathways.

11. The system of claim 1, wherein the support structure comprises flexible attachment arms extending from either side of the backing, thereby configuring the array of electrodes to wrap around and form a stable attachment with the spinal cord.

12. The system of claim 1, wherein the support structure comprises left and right support features that extend laterally from the backing and are configured to pass from the spinal cord to the surrounding dura of the patient at positions that are adjacent to left and right dentate ligaments, thereby supporting the array of electrodes in contact with the spinal cord such that the array moves with the spinal cord when the spinal cord moves within the patient's dura.

13. The system of claim 1, wherein the circuitry is configured and programmed for delivering electrical stimulation to target the subregion by activating selected combinations of the electrodes.

14. The system of claim 1, wherein the circuitry is configured and programmed to drive individual electrodes selectively so as to stimulate programmably preselected target regions of the spinal cord.

15. A method of preparing a subject for treatment of pain, comprising:
    obtaining a system comprising an electrode assembly and circuitry according to claim 1;
    forming an opening in the dura surrounding the subject's spinal cord;
    passing the electrode assembly through the opening and placing it so that the array of electrodes is in direct contact with the spinal cord at a position from which to deliver electrical stimuli to a targeted subregion of the spinal cord;
    securing the electrode assembly so that:
        (1) the CSF filled space is maintained, thereby separating the dura from the spinal cord, preventing mechanical constriction and obstruction of CSF flow between the electrode assembly and the dura; and
        (2) the array stays in place against the spinal cord as the spinal cord moves inside the dura;
    coupling the electrode assembly inside the dura to circuitry outside the dura through a lead fitting; and
    closing the dura around the lead fitting so as to form a watertight closure.

16. A method of treating pain in a subject, comprising delivering electrical stimuli to a targeted subregion of the spinal cord of the subject by way of a system according to claim 1 that has been implanted in the spinal canal inside the dura of the subject so that the array of electrodes is placed and secured in direct contact with the subject's spinal cord and maintains its position as the spinal cord moves inside the dura.

17. The method of claim 16, wherein the pain is associated in the subject with a musculo-skeletal disorder, a neoplasm, arthritic degeneration, a neurodegenerative disorder, or trauma.

18. A method of preparing a subject for treatment of pain, comprising:
    obtaining a system comprising an electrode assembly and circuitry according to claim 1; and
    implanting the electrode assembly inside the dura of the subject such that the electrodes in the array are placed in direct contact with the pial surface of the subject's spinal cord at a position from which to deliver electrical stimuli to a targeted subregion of the spinal cord; and
    securing the electrode assembly in place so that:
        (1) the CSF filled space is maintained, thereby separating the dura from the spinal cord, preventing mechanical constriction and obstruction of CSF flow between the electrode assembly and the dura; and
        (2) the array stays in place against the spinal cord as the spinal cord moves inside the dura.

19. The method of claim 18, further comprising coupling the electrode assembly with the circuitry, thereby configuring the electrodes for delivering the electrical stimuli to the targeted subregion.

20. A method of treating pain in a subject, comprising preparing the subject according to claim 19, and then delivering electrical stimuli to the targeted subregion of the spinal cord through the electrodes of the electrode assembly, thereby treating the pain.

21. An electrode array configured for implanting inside the dura that surrounds a patient's spinal cord and for delivering electrical stimulation directly to the spinal cord, comprising:
    (1) a curved backing having a curvature that is contoured to match the curvature of the spinal cord, and is sufficiently elastic to expand and contract with spinal cord movement; and
    (2) a plurality of electrodes projecting from inside the curvature of the backing, positioned so as to directly engage the spinal cord when the curved backing is conformed to the spinal cord;
    wherein the backing is configured for wrapping around the spinal cord, thereby securing the electrodes in contact with the spinal cord; and
    wherein the electrode array has a sufficiently thin profile and configuration such that when the array of electrodes is placed against the spinal cord inside the dura, the CSF filled space is maintained, thereby separating the dura from the spinal cord, preventing mechanical constriction and obstruction of CSF flow between the electrode array and the dura.

* * * * *